US008357526B2

(12) United States Patent
Keeler et al.

(10) Patent No.: US 8,357,526 B2
(45) Date of Patent: *Jan. 22, 2013

(54) **IDENTIFICATION, CHARACTERIZATION, AND APPLICATION OF *PSEUDOMONAS STUTZERI* (LH4:15), USEFUL IN MICROBIALLY ENHANCED OIL RELEASE**

(75) Inventors: Sharon Jo Keeler, Bear, DE (US); Robert D. Fallon, Elkton, MD (US); Edwin R. Hendrickson, Hockessin, DE (US); Linda L. Hnatow, Oxford, PA (US); Scott Christopher Jackson, Wilmington, DE (US); Michael P. Perry, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1283 days.

This patent is subject to a terminal disclaimer.

(21) Appl. No.: 12/105,769

(22) Filed: Apr. 18, 2008

(65) Prior Publication Data
US 2009/0263887 A1 Oct. 22, 2009

(51) Int. Cl.
*C02F 3/34* (2006.01)
*C10G 32/00* (2006.01)
*C12N 1/02* (2006.01)
*C12N 1/20* (2006.01)

(52) U.S. Cl. ........... 435/253.3; 435/252.4; 435/261; 435/262; 435/281; 435/822; 435/874

(58) Field of Classification Search ............ None
See application file for complete search history.

(56) References Cited

U.S. PATENT DOCUMENTS

| 5,877,014 | A | 3/1999 | Shetty et al. | |
|---|---|---|---|---|
| 6,087,155 | A | 7/2000 | York et al. | |
| 6,183,644 | B1 | 2/2001 | Adam et al. | |
| 6,541,240 | B1 | 4/2003 | Kilbane et al. | |
| 6,573,087 | B2 | 6/2003 | Lehr | |
| 7,708,065 | B2 * | 5/2010 | Hendrickson et al. | 166/246 |
| 7,776,795 | B2 * | 8/2010 | Keeler et al. | 507/201 |
| 2003/0008379 | A1 | 1/2003 | Bhosle et al. | |
| 2007/0092930 | A1 | 4/2007 | Lai et al. | |

FOREIGN PATENT DOCUMENTS

WO 95/31408 A1 11/1995

OTHER PUBLICATIONS

Banat, I. M., Biosurfactants Production and Possible Uses in Microbial Enhanced Oil Recovery and Oil Pollution Remediation: A Review, Bioresource Technology, Jan. 1, 1995, pp. 1-12, vol. 51, Elsevier Science Limited.
Bertoni, Giovanni et al., Analysis of the Gene Cluster Encoding Toluene/o-Xylene Monooxygenase from *Pseudomonas stutzeri* OX1, Applied and Environmental Microbiology, Oct. 1998, pp. 3626-3632, vol. 64, No. 10, American Society for Microbiology.
Bertoni, Giovanni et al., Cloning of the Genes for and Characterization of the Early Stages of Toluene and o-Xylene Catabolism in *Pseudomonas stutzeri* OX1, Applied and Environmental Microbiology, Oct. 1996, pp. 3704-3711, vol. 62, No. 10, American Society for Microbiology.
Martin-Gil, J. et al., *Shewanella putrefaciens* in a fuel-in-water emulsion from the Prestige oil spill, Antonie van Leeuwenhoek, Oct. 1, 2004, pp. 283-285, vol. 86, No. 3. Kluwer Academic Publishers.
Almeida, P.F. et al., Selection and Application of Microorganisms to Improve Oil Recovery, Engineering in Life Sciences, Aug. 1, 2004, pp. 319-325, vol. 4, No. 4.
International Search Report Dated Jul. 31, 2009, International Application No. PCT/US2009/040883.
International Preliminary Report on Patentability in corresponding PCT/US2009/040883 application mailed Oct. 28, 2010.
Rius et al., Clonal Population Structure of *Pseudomonas stutzeri*, a Species With Exceptional Genetic Diversity, J. Bacteriol., 2001, vol. 183:736-744.
Sikorski et al., Identification of Complex Composition, Strong Strain Diversity and Directional Selection in Local *Pseudomonas stutzeri* Populations From Marine Sediment and Soils, Environ. Microbiol., 2002, vol. 4:456-476.
Diijk et al., Anaerobic Oxidation of 2-Chloroethanol Under Denitrifying Conditions by *Pseudomonas stutzeri* Strain JJ, Appl. Microbiol. Biotechnol., 2003, vol. 63:68-74.
Criddle et al., Transformation of Carbon Tetrachloride by *Pseudomonas sp.* Strain KC Under Denitrification Conditions, Appl. Environ. Microbiol., 1990, vol. 56:3240-3246.
J. Lalucat, Biology of *Pseudomonas stutzeri*, Microbiol. Mol. Biol. Rev., 2006, vol. 70:510-547.
A. Viggiani et al., An Airlift Biofilm Reactor for the Biodegradation of Phenol by *Pseudomonas stutzeri* OX1, J. Biotechnol., 2006, vol. 123:464-477.
Altschul et al., Basic Local Alignment Search Tool, J. Mol. Biol., 1990, vol. 215:403-410.
W.R. Pearson, Comput. Methods Genome Res., Proc. Int. Symp., Meeting Date 1992, 111-120, Eds: Suhai, Sandor, Plenum Publishing, New Tork, NY, 1994 (Book Not Included).
Abeda, Isolation of Biotechnological Organisms From Nature, 1990, p. 117-140, McGraw-Hill Publishers (Book Not Included).
C. Moreno-Vivian et al., Prokaryotic Nitrate Reduction: Molecular Properties and Functional Distinction Among Bacterial Nitrate Reductases, J. Bacteriol., 1999, vol. 181:6573-6584.
R.D. Fallon et al., Anaerobic Biodegradation of Cyanide Under Methanogenic Conditions, Appl. Environ. Microbiol., 1991, vol. 57:1656-1662.
A.W. Drews, Manual of Hydrocarbon Analysis, 6th Edition, 1998, (Book Not Included).
V. Pruthi et al., Rapid Identification of Biosurfactant Producing Bacterial Strains Using a Cell Surface Hydrophobicity Technique, Biotechnol. Techniques, 1997, vol. 11:671-674.
J.D. Levi et al., MEOR Strategy and Screening Methods for Anaerobic Oil-Mobilizing Bacteria, Intl. Biores. J., 1985, vol. 1:336-344.

(Continued)

*Primary Examiner* — Debbie K Ware
(74) *Attorney, Agent, or Firm* — Scully, Scott, Murphy & Presser, P.C.

(57) ABSTRACT

The present disclosure relates to isolation and identification of unique *Pseudomonas stutzeri* strains that can grow on crude oil under denitrifying conditions and are useful in oil recovery.

17 Claims, 9 Drawing Sheets

OTHER PUBLICATIONS

Figure 1:
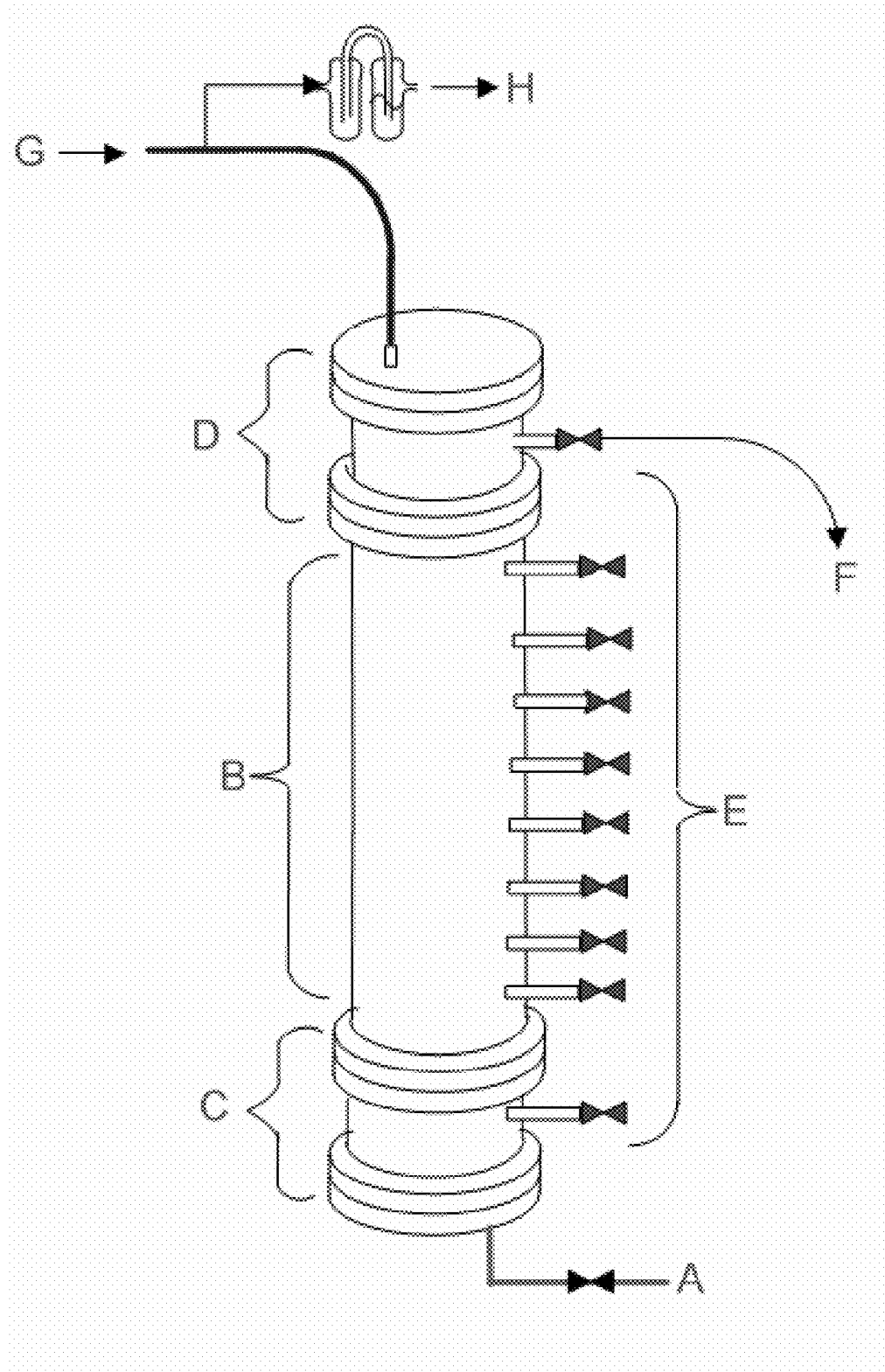

J.L. Bruce, Automated System Rapidly Identifies and Characterizes Microorganisms in Food, Food Technology, 1996, vol. 50:77-81.

M.R. Sethi, Fully Automated Microbial Characterization and Identification for Industrial Microbiologists, Am. Lab, 1997, vol. 5:31-35.

D.A. Newcombe et al., Bioremediation of Atrazine-Contaminated Soil by Repeated Applications of Atrazine-Degrading Bacteria, Appl. Microbiol. Biotechnol., 1999, vol. 51:877-882.

C. Barbeau et al., Bioremediation of Pentachlorophenol-Contaminated Soil by Bioaugmentation Using Activated Soil, Appl. Microbiol. Biotechnol., 1997, vol. 48:745-752.

H. Bredholt et al., Hydrophobicity Development, Alkane Oxidation, and Crude-Oil Emulsification in a *Rhodococcus* Species, Can. J. Microbiol., 2002, vol. 48:295-304.

* cited by examiner-

SEQUENCE LISTING

<160> NUMBER OF SEQ ID NOS: 10

<210> SEQ ID NO 1
<211> LENGTH: 20

```
<212> TYPE: DNA
<213> ORGANISM: artificial sequence
<220> FEATURE:
<223> OTHER INFORMATION: primer 1492R

<400> SEQUENCE: 1
cggttacctt gttacgactt                                              20

<210> SEQ ID NO 2
<211> LENGTH: 20
<212> TYPE: DNA
<213> ORGANISM: artificial sequence
<220> FEATURE:
<223> OTHER INFORMATION: primer 8F

<400> SEQUENCE: 2
agagtttgat ymtggctcag                                              20

<210> SEQ ID NO 3
<211> LENGTH: 22
<212> TYPE: DNA
<213> ORGANISM: artificial sequence
<220> FEATURE:
<223> OTHER INFORMATION: primer pr1f-1

<400> SEQUENCE: 3
acgtggcaaa gggtccgatc gc                                           22

<210> SEQ ID NO 4
<211> LENGTH: 20
<212> TYPE: DNA
<213> ORGANISM: artificial sequence
<220> FEATURE:
<223> OTHER INFORMATION: primer pr2r-1

<400> SEQUENCE: 4
gatcatgagc ggagcgacga                                              20

<210> SEQ ID NO 5
<211> LENGTH: 21
<212> TYPE: DNA
<213> ORGANISM: artificial sequence
<220> FEATURE:
<223> OTHER INFORMATION: primer pr3f-1

<400> SEQUENCE: 5
ggagcaagcg attaccgcta t                                            21

<210> SEQ ID NO 6
<211> LENGTH: 21
<212> TYPE: DNA
<213> ORGANISM: artificial sequence
<220> FEATURE:
<223> OTHER INFORMATION: primer pr4r-1

<400> SEQUENCE: 6
acttcccaac gcgccagata g                                            21

<210> SEQ ID NO 7
<211> LENGTH: 16
<212> TYPE: DNA
<213> ORGANISM: artificial sequence
<220> FEATURE:
<223> OTHER INFORMATION: primer M13 reverse

<400> SEQUENCE: 7
aacagctatg accatg                                                  16
```

<210> SEQ ID NO 8
<211> LENGTH: 17
<212> TYPE: DNA
<213> ORGANISM: artificial sequence
<220> FEATURE:
<223> OTHER INFORMATION: primer M13 forward

<400> SEQUENCE: 8
gtaaaacgac ggccagt                                                    17

<210> SEQ ID NO 9
<211> LENGTH: 2178
<212> TYPE: DNA
<213> ORGANISM: Pseudomonas stutzeri

<400> SEQUENCE: 9

| | | | | | |
|---|---|---|---|---|---|
| aattcttttc | ggcctcggac | atggcagctt | gaatggctgg | tccgagagca | tcccaggaac | 60 |
| caacgtcctg | agcccattga | gccatgatcg | cgccgtattg | cttcaccagg | gcagagcggg | 120 |
| cgcgttcggt | gtcggactgt | ttccagacgg | tgccaacagc | gcgtttgacg | agatcgtccc | 180 |
| agccgaagaa | ctggatcgca | tcgggcaccc | aggaagcacc | aaaggcatcg | agaggatccc | 240 |
| aacggccaac | agccagacga | tgttcgcgct | taggtctgac | ccgcacttcg | aggcgtaccc | 300 |
| agtccctagg | agcatccccg | ccttgctcga | acccttctc  | atagagcact | aggcggacgg | 360 |
| gtgaatcctt | ggatccgacg | tagagcgtgc | gagcctcacc | acggacccaa | tcgccctgct | 420 |
| ggttgatcgc | caagcggttg | tcctgagcga | actggatcag | agcagcggac | acagagtcga | 480 |
| aaaaccttc  | ttcctgccag | tcctcacaag | cgtcaaccct | ggttggcatg | tggggcttcc | 540 |
| cgaagctgcg | gagagcgtca | gcaagcacag | gcgactcatc | gctagttgtc | ttgcagttga | 600 |
| cgccgttctg | gcctccccag | cagacgtggc | aaagggtccg | atcgccgcga | cggacctgac | 660 |
| cgccgtacag | gtagccgttg | aggttcttgg | cgggcgccca | gtcggacaat | ggccacgctc | 720 |
| gcaagaggtg | ctccacgagg | ccggaatcct | ggggatcctg | gacgaggaca | gtcgactggt | 780 |
| accaatccca | ccgaatcatg | gctcaatccc | ttgatttaga | gcggctggaa | gagccttttag | 840 |
| aaggtttcgc | ggggcggg   | ggttgggtac | ctgaccccg  | tgttactaca | tggggtcgg  | 900 |
| aagccggttc | gagatccacg | ccagtctcga | ttttgtgcat | caaaagctga | aactggcggt | 960 |
| tggcttcccc | cgttgcgtta | accatctcat | tctgaaggcc | ctccgcaaca | gctcgaaggc | 1020 |
| ctgctttgac | ctgattagga | gcctcctggg | cggcctctag | aagcgagatc | gtgcgaccga | 1080 |
| tggatggggc | tatctcattc | agcagttcag | cgatcacagc | gcctcgtgtg | cggttctgga | 1140 |
| gacgggcaaa | gcgctcgatg | acctcatggg | tttctggctc | gagcgtgact | tggacgcgag | 1200 |
| gtttgacggt | tggcatgacg | tttccaggtg | gacacttatg | gccgaagtgt | ggcctaaggg | 1260 |
| tggacacctc | gtcaataggt | gaacactgac | gcgcttcgct | tgtcggctac | gtcatgccgg | 1320 |
| cgcgcccgta | cccctcgcta | cgctcgtagc | ccggacacgc | cgtcctgccg | cagctccaat | 1380 |
| gagaggcgat | gtttgtgttt | cctggtgaca | aacagacaaa | caggctcacg | aagaagcccc | 1440 |
| cggccgaggc | cgagatccga | ttcagattgg | taccgttttg | gctaatgcag | gatagccatg | 1500 |
| ctggtggcta | gtgctgcact | tccccctgga | cggctcgtcg | ctccgctcat | gatccgctca | 1560 |
| gggggaagta | tcaatggacg | cttggggcgg | tgacccagg  | gaattgcttg | agcaggtgac | 1620 |
| ctaccagctg | gaggacggca | ggggcagcgt | tctcgcccat | gccatctatc | ccgaagtagc | 1680 |
| tgctttgaca | gtgccgcag  | aagccgacct | tgaccagggc | gtgaggttct | ccccagatgg | 1740 |
| tggcgtgaac | ggttatccaa | cgctgacagg | atccgcactg | atggcggatc | cgcaggtcgc | 1800 |

```
tcggcttgat cttatcggac ggcatggttc tcctcaggac gcgctgtagg cgttgccacg    1860
aggcgcagtt cctttgcttg gttgatttgc gattgaagat cccggaagcc ttccaggatc    1920
ggttgaaaca tgagatcgag gccggcaacg aatgcacccg tgtcggtggg atagccctcc    1980
tgggggatgg cactgatcca ggtggtgacg agcctctggt aagcatcgag cgagcaattc    2040
aggttgtgga tgtcgtccaa ccaagcgagc ggcacgatag gatattcggt agtcatgtgg    2100
atctccttgc agatctgcgt gattagctgg tcactagggt tgcagcccca gtggccagcg    2160
cttttttccc tgtgcggg                                                  2178

<210> SEQ ID NO 10
<211> LENGTH: 2131
<212> TYPE: DNA
<213> ORGANISM: Pseudomonas stutzeri

<400> SEQUENCE: 10
agcttttcgg gctttcgccc gtaaagcggt actcgtcttg gacgtaccgg tagaagcgat      60
cccagtaggg cagagagtca aggggctcgt ccaagagcga ctcgggcact tcaacaccac     120
ggaacaggcc aaagctgttc agcaggcgct tacccttgag cagctgagcc gcgtgccagt     180
tgtccgccag cgtgaggtcg gagaacttca ccgcgtactt gaaaacctct aggaaaccct     240
cgctagggtc gcctgtgatg ggcctacaat cgacgatcat gctatcgccc gtgatcccgt     300
gccactcggc actgatcgcg ctctgagagg gcgcagaggc cgccagaacg atcatatggc     360
agtggggatg ccagcccttg cccttgttcg tcagttcgag cgtgtagacg ccccctcgg      420 ccttgcacag ctccgtccag gggtgaccac gcgaaccggc gttaaagttg cgcctgcggt     480
ccatgagttt gcgcagggag gaggtcaagt gcgcttgacg ctcggcgagg tcgtcaccgt     540
tcttcacggt cagcgtcagc aggtagggct tgaggtcggg acgctcggcg cggatgactt     600
cccaacgcgc cagataggcc ccgagggcct tggcgccacg cgaatggcg cagagcgggc      660 aaacgaggtg ctgcttgcag aaggaggcgt tgtgcaaccg taccttgccc acggtgaagt     720
actcccggaa gtgcaggtag ttgccacagc tggcgaggcc agtggcggtc tttgtcgctt     780
cgaccgatgg agcgccccga aggtgctcca gcatcgccag tgaccttgca tgcgcttggc     840
cgtagcgtgc taacctatcg ccgaagtttt cagcttcatc gacccctgtg aacgtcccgg     900
ccgccaagtc agacacgttc acgggggttt ctttttggc cattcgtggc cctccttccc      960
gtgccggcag cataccctgct gcgtgcactt tgttttctatg tatcaagtaa agaagcgccg    1020 accccccggca cacgtaccat tcagctgcgc tgaaaagccc gtgtgccgcg gcccggaagc    1080
catctgaggt tgatctacga agcagtgacg agctgaggct ttgcgccctg cgggatgaag    1140
tagccgacgc ttttgccgag cgcataaacg cccaccggga cgcgaacggt cttgttcatg    1200
gccgcctgaa acaggcgtgc gtcctcgacg ttgagggtga cgagttcgag cttgtgccca    1260
ccggtgggca tggggagctg gccgaggatc tgaaccttgt cccgaggatc aaacgcctcg    1320 ccggtttttct tcgatgtgcc gcccggctgg acgtacacgt tagcgacttg gccgcagagg    1380
gtgaacatgg cttcactcat cgctggagtc ctccagctct tcatcgtgag cagtccagag    1440
cgccacgatt tcctgtgacc acgccgcgcg gtcggcttcg gtcatcttgc tgccgatagc    1500
ggtaatcgct tgctccatcg cagcgccgat cagctcgaaa agcagttcct gtcgggacag    1560
ttcgagaacg tcggccacct tgtcgattgc agccacctgc ccttcggaa ggcgaacagt     1620 gacgccccgg taactggacg ggctgctgcg catcatctgc ttgatggcct gttcctgaac    1680
gcgatggttc acgaaatcgc tgacgctttc gtgagtgtta atgcgggtgc cttcaactac    1740
```

```
gcgattaatc atttgcctct cctgtgattt ttcaggcgaa tcatgcctga gtgcgcagtg    1800
attcttgacc ggtgcaggcc gaaaatcaag cggaaccaca gtccgagcag ggtttctacg    1860
ccttgggctt ttttcaagcg cgctaaaagc ccctccgggg gccctgccgg gggcccctcg    1920 ccgggggggca ggcggtcagg gggaagagcg cccccctgacc accagccaga gggtttcttg  1980
ttcgtgcagg gtcaagggtg cgcttcgccc gtgcctccgt tcatccgggg gatggagcgc    2040
cccccggacg agccggggggc gcggcccctg acctatacgg gccgtgcgtg ctgatgggac   2100
gccggaggcg gctcagaggc aggtgcggaa a                                   2131
```

IDENTIFICATION, CHARACTERIZATION, AND APPLICATION OF *PSEUDOMONAS STUTZERI* (LH4:15), USEFUL IN MICROBIALLY ENHANCED OIL RELEASE

FIELD OF INVENTION

This disclosure relates to the field of environmental microbiology and modification of heavy crude oil properties using microorganisms. More specifically, pure microorganisms are used under denitrifying conditions to modify the properties of heavy crude oil in order to enhance the recovery of the crude oil from its underground reservoir.

BACKGROUND OF THE INVENTION

The challenge to meet the ever increasing demand for oil includes increasing crude oil recovery from heavy oil reservoirs. This challenge has resulted in expanding efforts to develop alternative cost efficient oil recovery processes (Kianipey, S. A. and Donaldson, E. C. 61$^{st}$ Annual Technical Conference and Exhibition, New Orleans, La., USA, Oct. 5-8, 1986). Heavy hydrocarbons in the form of petroleum deposits and oil reservoirs are distributed worldwide. These oil reservoirs are measured in the hundreds of billions of recoverable barrels. Because heavy crude oil has a relatively high viscosity, it is essentially immobile and cannot be easily recovered by conventional primary and secondary means.

Microbial Enhanced Oil Recovery (MEOR) is a methodology for increasing oil recovery by the action of microorganisms (Brown, L. R., Vadie, A. A., Stephen, O. J. SPE 59306, SPE/DOE Improved Oil Recovery Symposium, Oklahoma, Apr. 3-5, 2000). MEOR research and development is an ongoing effort directed at discovering techniques to use microorganisms to modify crude oil properties to benefit oil recovery (Sunde. E., Beeder, J., Nilsen, R. K. Torsvik, T., SPE 24204, SPE/DOE 8$^{th}$ Symposium on enhanced Oil Recovery, Tulsa, Okla., USA, Apr. 22-24, 1992).

Methods for identifying microorganisms useful in MEOR processes have been described. These methods require identification of samples drawn from an oil well or reservoir comprising a consortium of microorganisms and enrichment or evolution of populations in the sample under specific conditions with a defined nutrient medium (U.S. Patent Application No. 2007/0092930A1). Thus, there is a need for developing methods to: 1) identify microorganisms that can grow in or on oil under anaerobic denitrifying conditions by selection of pure isolates from enrichment of indigenous microorganisms; 2) screen isolates for properties that might be useful in oil modification or interactions and 3) use said identified microorganisms, in a cost-efficient way, to improve oil recovery.

The microorganism described herein has been identified as a strain of *Pseudomonas stutzeri*. *Pseudomonas stutzeri* belongs to a broad category of denitrifying bacteria that is found in, and adaptable to, many environments. *Pseudomonas stutzeri* are grouped into genomovars based on DNA-DNA hybridization. Typing by 16S rDNA gene sequence has been in agreement with the hybridization typing. However, *Pseudomonas stutzeri* is considered to have high genetic mutation rates (Rius, Nuria, R., et al., J. Bacteriol., 183, 736-744, 2001) and is easily transformed in its natural environment (Sikorski, J., et al., Environ. Microbiol., 4, 456-476, 2002). *Pseudomonas stutzeri* strain LH4:15 16S rDNA gene has 100% homology to a *Pseudomonas stutzeri* (strain 24a97) isolated from soil contaminated with mineral oil near a filling station in Northern Germany (Sikorski, J. et al., supra). Other *Pseudomonas stutzeri* strains have been found in association with oil and petroleum and were seen to degrade alkanes. Aerobic cleavage of C—N bonds in oil compounds by *Pseudomonas stutzeri* strains has been disclosed (U.S. Pat. No. 6,541,240B1).

Strains of *Pseudomonas stutzeri* have been used in bioremediation processes. Crude oil and petroleum product bioremediation from water and soil by a consortium that contains *Pseudomonas stutzeri* is described in WO 95/031408A1. *Pseudomonas stutzeri* strain JJ anaerobically degrades 2-chloroethanol under denitrifying conditions (Diijk, J. A., et al., Appl. Microbiol. Biotechnol., 63, 68-74, 2003). Strain KC was isolated from an aquifer and transforms carbon tetrachloride to carbon dioxide, formate and other non-volatile compounds anaerobically (Criddle, C. S., et al., Appl. Environ. Microbiol., 56, 3240-3246, 1990). Aerobic biodegradation of aromatic hydrocarbons has been widely observed in *Pseudomonas stutzeri* strains, but observation of anaerobic degradation has been limited (Lalucat, J., et al., Microbiol. Mol. Biol. Rev. 70: 510-547, 2006). *Pseudomonas stutzeri* has been used for bioremediation of other xenobiotic, toxic environmental pollutants, e.g., nitrogen compounds, biocides, high molecular weight polyethylene glycols, and metals.

*Pseudomonas stutzeri* is also known to form biofilms (Viggiani, A., et al., J. Biotechnol. 123, 464-77, 2006). *Pseudomonas stutzeri* biofilm has been used to remove oxidized selenium from water (U.S. Pat. No. 6,183,644B1), and *Pseudomonas stutzeri* (accession #MCMRD-AB-001) is disclosed as a biofilm for the production of xylanase (US Patent Application No. 20030008379).

SUMMARY OF THE INVENTION

The invention relates to the identification of a microorganism from production water samples obtained from an oil reservoir. A screening protocol was developed to identify microbes capable of growth under denitrifying conditions using oil or oil components as the sole source of carbon. These microbes could be grown in situ in an oil reservoir for enhancement of oil recovery. Growth of the microorganisms, and specifically the pure cultures described herein, in an oil well or reservoir enhances economical recovery of oil.

The particular culture described herein is *Pseudomonas stutzeri* strain LH4:15. To differentiate strain *Pseudomonas stutzeri* LH4:15 from other known *Pseudomonas stutzeri* strains with homologous 16S rDNA sequences, LH4:15 and homologous *Pseudomonas stutzeri* strains were analyzed for the presence of extrachromosomal plasmids. As described in Examples 10 and 11, *Pseudomonas stutzeri* LH4:15 contains a set of two plasmids: plasmid LH4:15 pMP1 has partial identity (496/712, 69%) to *Pseudomonas stutzeri* S-47 plasmid p47S of unknown function, and plasmid LH4:15 pMP2 has partial identity (815/1019, 79%) to *Pseudomonas putida* plasmid pPP81 repA gene, ORFB, ORFC and ORFD. These plasmids were not detected in other *Pseudomonas stutzeri* strains that were 100% homologous within the 16S rDNA sequence. Further, ribotyping confirmed that the genomic sequences surrounding the 16S and 23 rDNA genes in LH4:15 are substantially different from tested *Pseudomonas stutzeri* strains underlining the uniqueness of strain *Pseudomonas stutzeri* LH4:15.

Thus, one aspect relates to an isolated microorganism designated as bacterial isolate *Pseudomonas stutzeri* LH4:15 (ATCC No. PTA-8823).

Another aspect relates to an oil recovery enhancing composition comprising: a) *Pseudomonas stutzeri* LH4:15

(ATCC No. PTA-8823); b) one or more electron acceptors; and c) at least one carbon source.

A further aspect relates to a method for improving oil recovery from an oil reservoir comprising: a) providing a composition comprising a bacterial isolate *Pseudomonas stutzeri* LH4:15 (ATCC No. PTA-8823), and minimal medium comprising simple nitrates capable of promoting the growth of said isolate; and b) inoculating said reservoir with the composition of (a); wherein growth of said isolate, under denitrifying conditions, in the oil reservoir promotes improved oil recovery.

An additional aspect relates to a method for promoting hydrocarbon bioremediation comprising applying bacterial isolate *Pseudomonas stutzeri* LH4:15 (ATCC No. PTA-8823) to an area contaminated with hydrocarbons.

Another aspect relates to a method for promoting oil pipeline maintenance comprising applying bacterial isolate *Pseudomonas stutzeri* LH4:15 (ATCC No. PTA-8823) to an oil pipeline.

BRIEF DESCRIPTION OF FIGURES AND SEQUENCES OF THE INVENTION

The following sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions. The symbols and format used for nucleotide and amino acid sequence data comply with the rules set forth in 37 C.F.R. §

TABLE 1

DESCRIPTION OF THE PRIMERS USED IN THE INVENTION

| Description | SEQ ID NO | NUCLEOTIDE SEQUENCE |
|---|---|---|
| Primer 1492R | SEQ ID NO: 1 | CGGTTACCTTGTTACGACTT |
| Primer 8F | SEQ ID NO: 2 | AGAGTTTGATYMTGGCTCAG |
| Primer-pr1f-1 forward SEQ walking | SEQ ID NO: 3 | ACGTGGCAAAGGGTCCGATCGC |
| Primer-pr2f-1 reverse SEQ walking | SEQ ID NO: 4 | GATCATGAGCGGAGCGACGA |
| Primer-pr3f-1 forward SEQ walking | SEQ ID NO: 5 | GGAGCAAGCGATTACCGCTAT |
| Primer-pr4f-1 forward SEQ walking | SEQ ID NO: 6 | ACTTCCCAACGCGCCAGATAG |
| Primer M13 reverse | SEQ ID NO: 7 | AACAGCTATGACCATG |
| Primer M13 forward | SEQ ID NO: 8 | GTAAAACGACGGCCAGT |

SEQ ID NO:9—plasmid LH4:15 pMP1
SEQ ID NO:10—plasmid LH4:15 pMP2

Applicants made the following biological deposits under the terms of the Budapest Treaty on the International Recognition of the Deposit of Microorganisms for the Purposes of Patent Procedure:

TABLE 2

INFORMATION ON DEPOSITED STRAINS

| Depositor Identification Reference | International Depository Designation | Date of Deposit |
|---|---|---|
| *Pseudomonas stutzeri* LH4:15 | ATCC No. PTA-8823 | Dec. 4, 2007 |
| *Shewenella putrefaciens* LH4:18 | ATCC No. PTA-8822 | Dec. 4, 2007 |

FIG. 1. Schematic of an acrylic column reactor used for enrichment of oil consuming strains.

Figure 2:
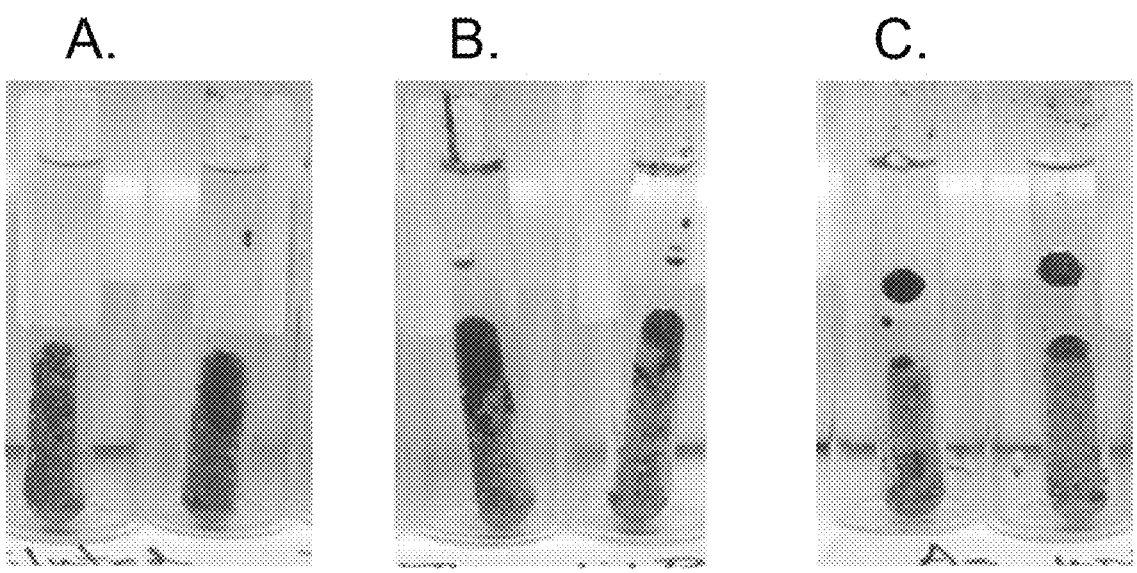

FIG. 2. A micro sand column oil release assay showing release of oil droplets. A. Control (no release); B. Droplets on surface (partial release); C. Oil in pipet neck (full release).

Figure 3:
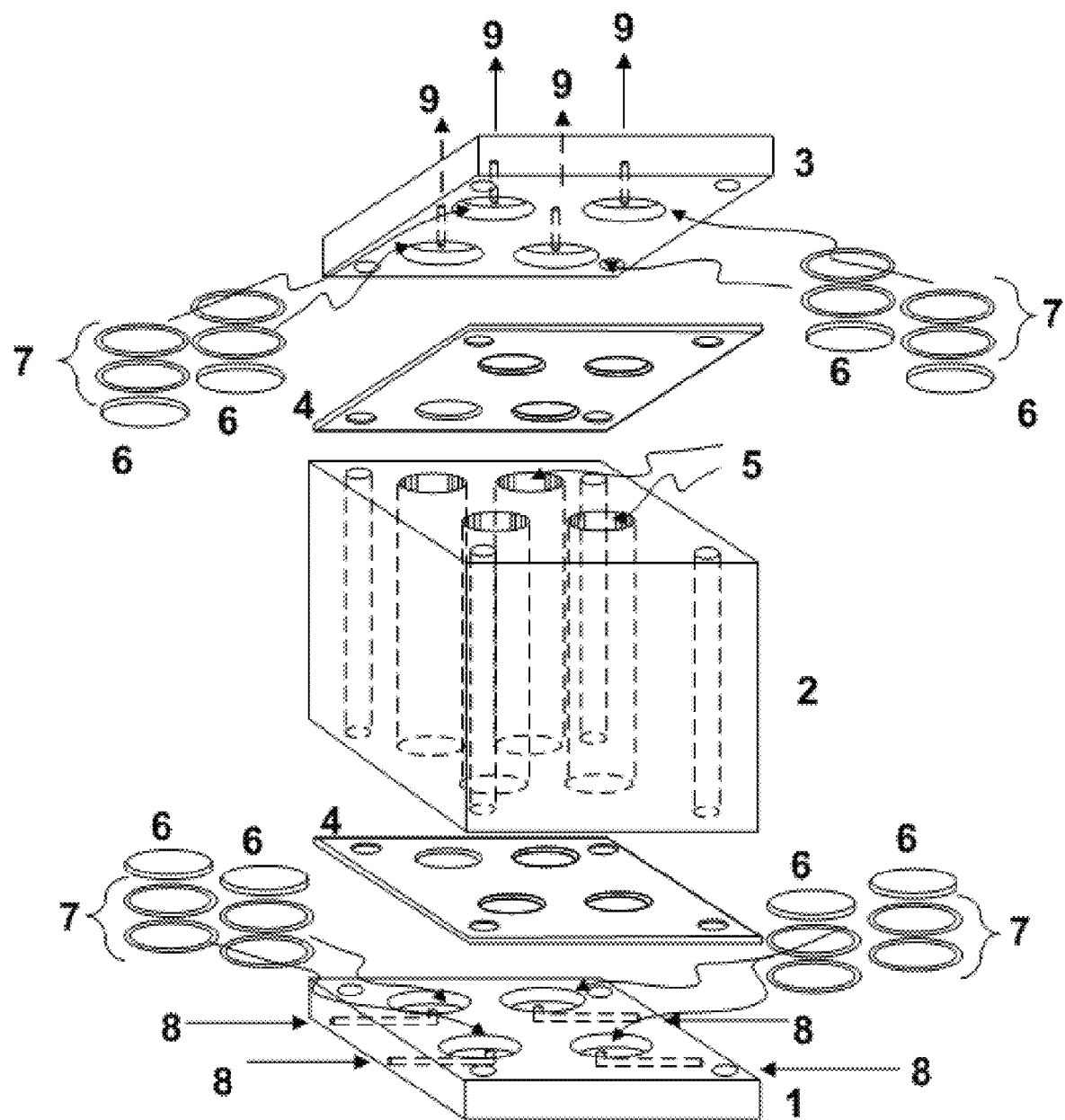

FIG. 3. Construction of mini sandpack column for oil release.

Figure 4:
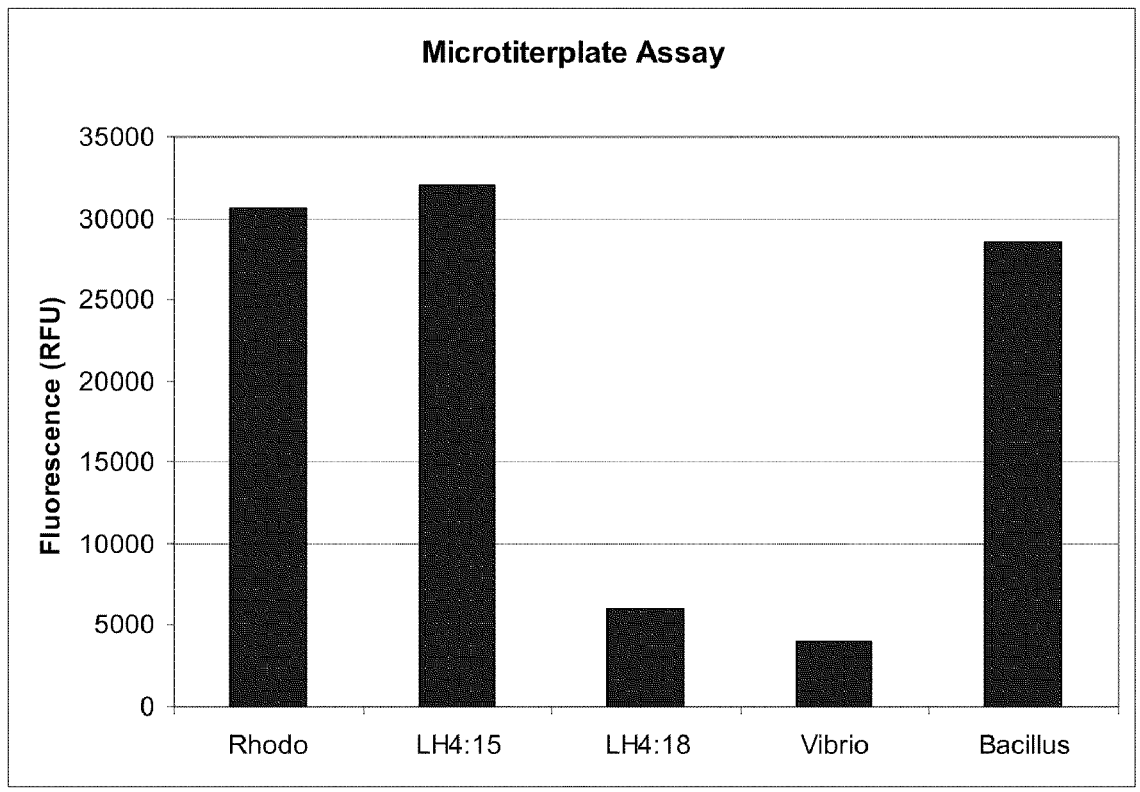

FIG. 4. A graph showing production of fluorescence of hydrophobic cell surfaces by various strains tested in a microtiter plate assay.

Figure 5:
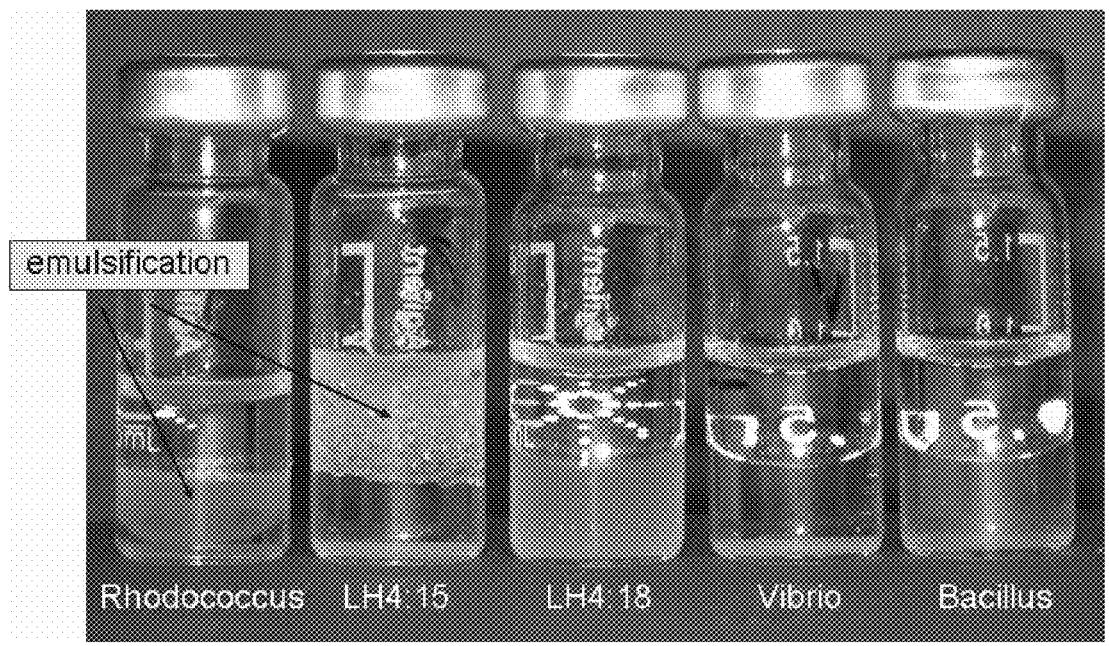

FIG. 5. Shows a stable oil-in-water emulsification for the *Rhodococcus* (control) sample and a stable water-in-oil emulsification for LH 4:15 indicating the presence of bioemulsifiers in these samples.

FIG. 6A. Shows screening of bacterial isolates in PPGAS medium, biofilm formed throughout the entire well.

FIG. 6B. Shows screening of bacterial isolates biofilm formed on glass beads in the presence of acetate.

Figure 7:
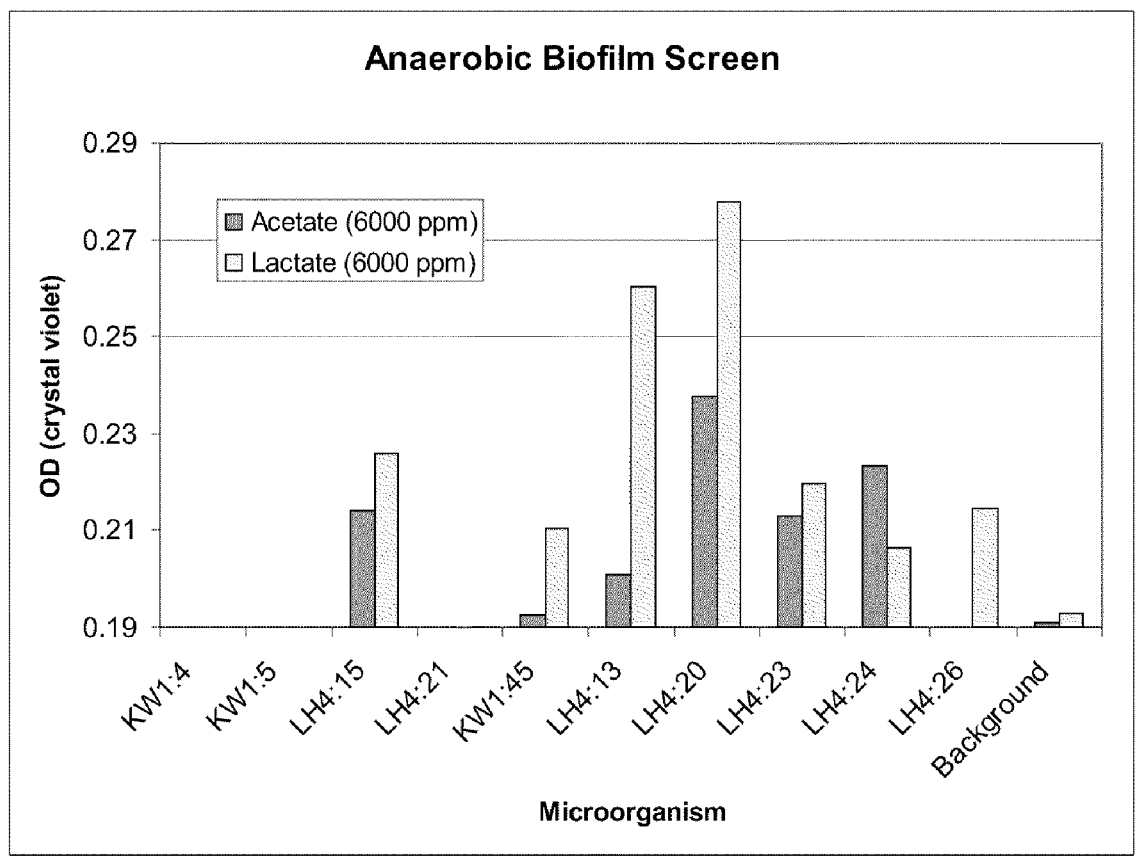

FIG. 7. A graph showing a quantitative screen for anaerobic biofilm formation.

Figure 8:
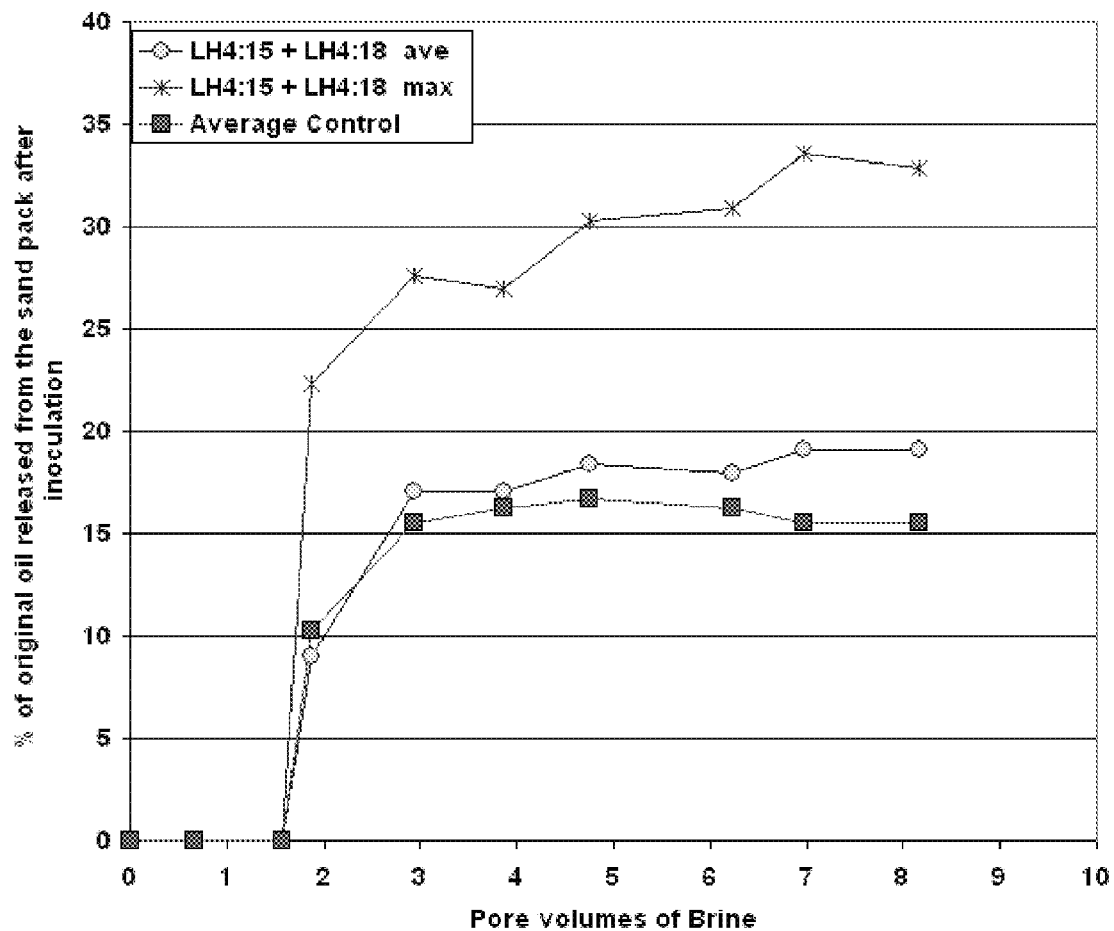

FIG. 8. A graph showing a mini sandpack oil release assay using *Pseudomonas stutzeri* and *Shewanella putrefaciens*.

Figure 9:
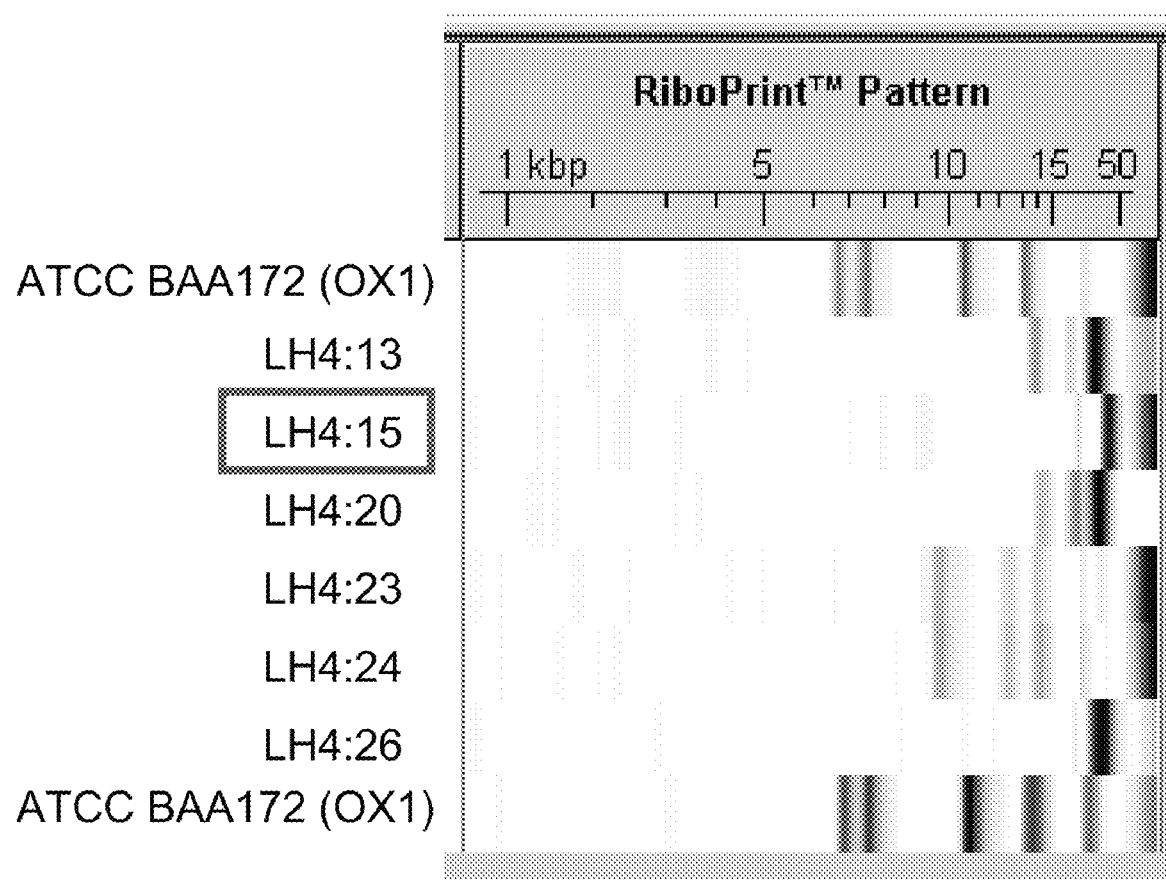

FIG. 9. Results of Riboprinter analysis of various *Pseudomonas stutzeri* strains.

DETAILED DESCRIPTION OF THE INVENTION

The invention relates to the identification of a previously unknown microorganism from production water samples obtained from an oil reservoir. A screening protocol was developed to identify microbes capable of growth under denitrifying conditions using oil or oil components as the sole source of carbon. These microbes could be grown in situ in an oil reservoir for enhancement of oil recovery.

The following definitions are provided for the special terms and abbreviations used in this application:

The term "PCR" refers to Polymerase chain reaction.

The term "dNTPs" refers to Deoxyribonucleotide triphosphates.

The term "ASTM" refers to the American Society for Testing and Materials.

The abbreviation "ATCC" refers to American Type Culture Collection International Depository, Manassas, Va., USA. "ATCC No." refers to the accession number to cultures on deposit with ATCC.

The term "environmental sample" means any sample exposed to hydrocarbons, including a mixture of water and oil. As used herein environmental samples include water and oil samples that comprise indigenous microorganisms useful for phylogenetic mapping of genera present in a given sampling area.

The terms "oil well" and "oil reservoir" may be used herein interchangeably and refer to a subterranean or sea-bed formation from which oil may be recovered.

The term "improving oil recovery" refers to the use of hydrocarbon-utilizing microorganisms, which are endemic in petroleum reservoirs, where they occur naturally using hydrocarbons as a food source. As a result of this process, through excretion of bio-products such as alcohols, gases, acids, surfactants and polymers, hydrocarbon-utilizing microorganisms can change the physico-chemical properties of the crude oil. Changed physico-chemical properties are, e.g., those described under the term "modifying the environment of oil well", infra.

The term "growing on oil" means the microbial species are capable of metabolizing hydrocarbons or other organic components of crude petroleum as a nutrient to support growth.

The terms "denitrifying" and "denitrification" mean reducing nitrate for use in respiratory energy generation.

The term "sweep efficiency" means the ability of injected water to 'push' oil through a geological formation toward a producer well. One problem that can be encountered with waterflooding operations is the relatively poor sweep efficiency of the water, i.e., the water can channel through certain portions of the reservoir as it travels from the injection well(s) to the production well(s), thereby bypassing other portions of the reservoir. Poor sweep efficiency may be due, for example, to differences in the mobility of the water versus that of the oil, and permeability variations within the reservoir which encourage flow through some portions of the reservoir and not others.

The term "pure culture" means a culture derived from a single cell isolate of a microbial species. The pure cultures specifically referred to herein include those that are publicly available in a depository. Additional pure cultures are identifiable by the methods described herein.

The term "biofilm" means a film or "biomass layer" of microorganisms. Biofilms are often embedded in extracellular polymers, which adhere to surfaces submerged in, or subjected to, aquatic environments.

The term "simple nitrates" and "simple nitrites" refer to nitrite ($NO_2$) and nitrate ($NO_3$).

"Injection Water" means water used to inject into oil reservoirs for secondary oil recovery.

The term "modifying the environment of oil well" includes one or more of 1) altering the permeability distribution of the subterranean formation (sweep efficiency), (2) producing biosurfactants which decrease surface and interfacial tensions, (3) mediating changes in wettability, (4) producing polymers that improve the oil/water mobility ratio; (5) generating gases (predominantly $CO_2$) that increase formation pressure; and (6) reducing oil viscosity.

The term "phylogenetic typing", "phylogenetic mapping", or "phylogenetic classification" may be used interchangeably herein and refer to a form of classification in which microorganisms are grouped according to their ancestral lineage. The methods herein are specifically directed to phylogenetic typing on environmental samples based on 16S Ribosomal DNA (rDNA) sequencing. In this context, a full 1400 base pair (bp) length of the 16S rDNA gene sequence is generated using primers identified herein and compared by sequence homology to a database of known rDNA sequences of known microorganisms. This comparison is then used for identification of pure cultures for use in enhanced oil recovery.

The term "ribotyping" means fingerprinting of genomic DNA restriction fragments that contain all or part of the genes coding for the 16S and 23S rRNA.

The term "microbial species" means distinct microorganisms identified based on their physiology, morphology and phylogenetic characteristics using 16S rDNA sequences.

The abbreviation "NCBI" refers to the National Center for Biotechnology Information.

The abbreviation "rDNA" refers to Ribosomal Deoxyribonucleic Acid.

The term "rDNA typing" means the process of utilizing the sequence of the gene coding for 16S rDNA to obtain the "closest relative" microbial species by homology to rDNA sequences maintained in several international databases.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215, 403-410, 1990), DNASTAR (DNASTAR, Inc., Madison, Wis.), and the FASTA program incorporating the Smith-Waterman algorithm (Pearson, W. R., *Comput. Methods Genome Res.,* Proc. Int. Symp, Meeting Date 1992, 111-120, Eds: Suhai, Sandor, Plenum Publishing, New York, N.Y., 1994). Within the context of this application, it will be understood that, where sequence analysis software is used for analysis, the results of the analysis will be based on the "default values" of the program referenced, unless otherwise specified. As used herein "default values" will mean any set of values or parameters which originally load with the software when first initialized.

Additional abbreviations used in this application are as follows: "hr" means hour(s), "min" means minute(s), "day" means day(s), "mL" means milliliters, "mg/ml" means milligram per milliliter, "L" means liters, "L" means microliters, "mM" means millimolar, "µM" means micromolar, "nM" means nano molar, "g/l" means microgram per liter, "pmol" means picomol(s), "° C." means degrees Centigrade, "° F." means degrees Fahrenheit, "bp" means base pair, "bps" means base pairs, "mm" means millimeter, "ppm" means part per million, "g/l" means gram per liter, "ml/min" means milliliter per minute, "ml/hr" means milliliter per hour, "cfu/ml" means colony forming units per milliliter, "g" means gram, "mg/L" means milligram per liter, "Kev" means kilo or thousands of electron volts, "psig" means per square inch per gram, "LB" means Luria broth, "rpm" means revolution per minute.

Growth of Microorganisms

Techniques for growth and maintenance of anaerobic cultures are described in "Isolation of Biotechnological Organisms from Nature", (Labeda, D. P. ed. 117-140, McGraw-Hill Publishers, 1990). Anaerobic growth is measured by nitrate depletion from the growth medium over time. Nitrate is utilized as the primary electron acceptor under the growth conditions used herein. The reduction of nitrate to nitrogen has been previously described (Moreno-Vivian, C., et al., J. Bacteriol., 181, 6573-6584, 1999). In some cases nitrate reduction processes lead to nitrite accumulation which is subsequently further reduced to nitrogen. Accumulation of nitrite is therefore also considered evidence for active growth and metabolism by microorganisms.

Ion Chromatography

To quantitate nitrate and nitrite ions in aqueous media, Applicants used an ICS2000 chromatography unit (Dionex, Banockburn, Ill.). Ion exchange was accomplished on an AS15 anion exchange column using a gradient of 2 to 50 mM potassium hydroxide. Standard curves using known amounts of sodium nitrite or sodium nitrate solutions were generated and used for calibrating nitrate and nitrite concentrations.

Screening to Discover Environmental Isolates Capable of Growth on Oil Components A screening protocol to discover novel pure cultures capable of growth on and/or modification of petroleum components was implemented as follows:

Samples from Oil Reservoir Production Water.

Water samples were obtained from production and injection well heads as mixed oil/water liquids in glass 1.0 L brown bottles, filled to the top, capped and sealed with tape to prevent gas leakage. Gas from inherent anaerobic processes sufficed to maintain anaerobic conditions during shipment. The bottles were shipped in large plastic coolers filled with ice blocks to the testing facilities within 48 hr of sampling.

Column Enrichment

Column reactors were used to develop enrichment cultures from industrial and environmental samples to select for a diversity of organisms that would grow on oil for use in MEOR. The use of column reactors has previously been reported (Fallon, R. D., et al., *Appl. Environ. Microbiol.*, 57, 1656-1662, 1991). An acrylic column reactor (3 inch diameter by 24 inch length, shown in FIG. 1) was used. The column had 9 side ports (FIG. 1 (E)), and each side port had a ⅛ inch National Pipe Thread (NPT) female threads tapped into it. A male ⅛ inch pipe to ⅛ female swagelock tube fitting adapter (Swagelok Company, Solon, Ohio) was mounted into this threaded hole. Into the ⅛ inch tube end of this fitting was mounted a septum so that a syringe needle could be used to later sample the column. This mounting was made air tight as evidenced by the fact that no water leaked when the column was filled with water. The column was mounted vertically as indicated in FIG. 1. Each of the fittings was located along the side of the column at intervals of 2 inches height. At both ends of this column, common 80 mesh screen and ordinary glass wool were mounted and later used (as described below) to contain ocean sand in the column. At the top and bottom of the column were empty sections (FIG. 1, (C) and (D)). Each of these empty sections was 3 inches long and 3 inches in diameter. Holes were machined into each of these empty sections and ⅛ inch NPT female threads were cut and a male ⅛ inch pipe to ⅛ female swagelock tube fitting adapter (Swagelok Company) was mounted into this threaded hole. The port at the bottom empty section was connected to a syringe pump via ⅛ inch diameter stainless steel tubing (FIG. 1 (A)). The port from the top empty section overflowed (FIG. 1 (F)) and was connected to a collection container that was blanketed with nitrogen gas. The head space of this top section was vented to a nitrogen purged bubbler (FIG. 1, (G) and (H)). The top empty section of the column was temporarily removed and Ocean Sand (SX0076-1, LOT#46257714, EMD Chemicals Inc, Gibbstown, N.J.) was poured into the column so that it filled about 50% of the column. The sand was held in place by the glass wool and 80 mesh screen described above.

Crude oil from the Alaskan North Slope was used in Examples 2-5. This same crude oil batch was distilled following ASTM method 2892 ("*Manual on Hydrocarbon Analysis: 6th Edition*", A. W. Drews, editor, Printed by ASTM, 100 Barr Harbor Drive, West Conshohocken, Pa., 19428-2959, 1998). A portion of the still bottoms collected at a temperature of >610° F. (>321.1° C.) was used in a subsequent distillation following the ASTM method 5236 ("Manual on Hydrocarbon Analysis: 6th Edition", supra). About 400 g of the still bottoms collected at >1005° F. (>540.6° C.) from this distillation was dissolved in 100 g of toluene to make a flowable solution. This solution was poured onto the sand that was loaded in the bottom half of the column. Additional fresh ocean sand was then added to fill the column, and the >610° F. (>321.1° C.) still bottom collected from the ASTM 2892 distillation was poured onto this portion of fresh sand. The top empty section was replaced. The ⅛ tubing attached to the bottom section (FIG. 1 (A)) was disconnected from the syringe pump and connected instead to a source of low pressure (5 psig) nitrogen. Nitrogen was blown in through this ⅛ inch tubing attached to the bottom of the column for 4 days to evaporate any toluene. At the end of this four day period, the ⅛ inch tubing (FIG. 1 (A)) was disconnected from the nitrogen source and the syringe pump was reattached. Using the syringe pump and ⅛ inch tubing attached to the bottom of the column, the column was fed and saturated with a complete medium containing nitrate with composition essentially as in Table 2 except the base salts were 60 mg/L $CaCl_2.2H_2O$; 400 mg/L $MgSO_4.7H_2O$; 400 mg/L KCl; 40 mg/L $NaH_2PO_4$; 500 mg/L $NH_4Cl$; 2 g/L $NaHCO_3$; 400 mg/L $NaNO_3$; and 3 g/L NaCl. The column was then inoculated with water collected from the oil well production and water injection wells from Alaska North Slope oil fields. After inoculation, the column was allowed to sit for a week. After this period, the complete medium with nitrate was continuously fed at a rate of 1 ml/hr. Samples were periodically taken using syringes piercing through the septum sealed sampling ports (FIG. 1 (E)) described above, along the side of the column. In this manner, microbes were harvested for use in subsequent enrichment cultures. The microorganism mixes enriched in these reactors were used to isolate strains that grow either on oil or in the presence of oil. Culture LH4:18 was derived by taking samples from the lower ports on this column at 6 months post inoculation, diluting ×1,000 and streaking on standard Luria Broth (LB, Teknova, Hollister, Calif.) agar plates. Isolated colonies were selected for subsequent screening by 16S rDNA typing and oil release tests.

Direct Colony rDNA Sequence Analysis

Genomic DNA from bacterial colonies was isolated by diluting bacterial colonies in 50 μL of water. Diluted colony DNAs were amplified with Phi 29 DNA polymerase prior to sequencing (GenomiPHI Amplification Kit GE Life Sciences, New Brunswick, N.J.). An aliquot (1.0 μL) of the diluted colony was added to 9.0 μL of the Lysis Reagent (from the GenomiPHI Amplification Kit) and heated to 95° C. for 3.0 min followed by immediate cooling to 4° C. 9.0 μL of Enzyme Buffer and 1.0 μL of Phi 29 enzyme were added to each lysed sample followed by incubation at 30° C. for 18 hr. The polymerase was inactivated by heating to 65° C. for 10 min followed by cooling to 4° C.

DNA sequencing reactions were set up as follows: 8.0 μL of GenomiPHI amplified sample were added to 8.0 μL of BigDye v3.1 Sequencing reagent (Applied Biosystems, Foster City, Calif.) followed by 3.0 μL of 10 μM primers SEQ ID NOs: 1 and 2 (prepared by Sigma Genosys, Woodlands, Tex.), 4.0 μL of 5× BigDye Dilution buffer (Applied Biosystems) and 17 μL Molecular Biology Grade water (Mediatech, Inc., Herndon, Va.).

Sequencing reactions were heated for 3.0 min at 96° C. followed by 200 thermocycles of (95° C. for 30 sec; 55° C. for 20 sec; 60° C. for 2 min) and stored at 4° C. Unincorporated dNTPs were removed using Edge Biosystems (Gaithersburg, Md.) clean-up plates. Amplified reactions were pipetted into one well of a pre-spun 96 well clean up plate. The plate was centrifuged for 5.0 min at 5,000×g in a Sorvall RT-7 (Sorvall, Newtown, Conn.) at 25° C. The cleaned up reactions were placed directly onto an Applied Biosystems 3730 DNA sequencer and sequenced with automatic basecalling.

Each of the assembled rDNA sequences was compared to the NCBI rDNA database (~260,000 rDNA sequences) using the BLAST algorithm (Altschul et al., supra). The primary hit was used as an identifier of the most closely related known species identification. The initial screen using the rDNA colony direct sequencing reduced the number of colonies to be carried through further screening by 20 fold. The unique isolate set was then used to screen for growth on oil as a sole carbon source under denitrifying conditions.

Micro Sand Column Oil Release Test

Isolated bacterial strains were examined using a micro sand column assay to visualize oil release. A micro sand column consisted of an inverted glass Pasteur pipet containing sea sand (EMD chemicals, La Jolla, Calif.) which has been coated with crude oil and allowed to age for at least one week. Specifically, 280 mL of sterile sand and 84 mL of sterilized oil were combined in an anaerobic environment. The mixture was stirred for 5 min twice each day and allowed to age for six days under nitrogen. The barrels of glass Pasteur pipets were cut to half height and autoclaved. The cut end of the pipet was plunged into the sand/oil mix and the core filled to about 1.0 inch. The cut end of the pipet containing the oil/sand mixture was then placed into a glass test tube containing microbial cultures. The apparatus was sealed inside glass vials in an anaerobic environment, and the oil release from the sand observed in the tapered end of each pipet (FIG. 2). Oil released from the sand collects in the narrow neck of the Pasteur pipets or as droplets on the surface of the sand layer. Cultures which enhanced release of oil over background (sterile medium) were presumed to have altered the interaction of the oil with the sand surface and could potentially act to enhance oil recovery in a petroleum reservoir.

Screening Strains for Hydrophobicity

The method used was a modification of a procedure which indirectly measures hydrophobicity through the attachment of microbes to polystyrene plates (Pruthi, V. and Cameotra, S., *Biotechnol. Techniques,* 11, 671-674, 1997). Bacterial cultures were grown in 20 mL Marine Broth 2216 (Difco, B D Biosciences, San Jose, Calif.) to an approximate $OD_{600}$ of 1. Aliquots of cultures (10 µl) were spotted into the wells of a polystyrene ProxiPlate 96-F (PerkinElmer Life Sciences, Boston, Mass.) and incubated at room temperature for 2 min. Samples were rinsed twice with 100 µL sterile water and air dried. Adhered cells were fluorescently stained by adding 50 µl of a 1:500 dilution of Syto9 Component A (BacLight Kit, Molecular Probes, Eugene, Oreg.) into each well and incubating in the dark at room temperature for 8 min. Wells were then washed two times with 100 µL sterile water. Another 100 µL water was added to each well, and fluorescence intensity was measured under 480 nm wavelength in a Victor3 1420 Multilabel Plate Reader (Perkin Elmer Life Sciences).

Screening Strains for Emulsification of Hexadecane

Microorganisms synthesize a wide variety of biosurfactants and bioemulsifiers that lower surface and interfacial tensions and produce stable emulsions. An emulsification test was developed based on a modification of the bacterial adhesion to hydrocarbons (BATH) test as described by Pruthi and Cameotra (*Biotechnology Techniques,* 11, 671-674, 1997). Aliquots of the bacterial cultures (500 µL) were mixed with 500 µL hexadecane in a sealed vial and agitated using a Vortex mixer at high speed for 1 min. Hexadecane emulsification was monitored over time. Those bacterial cultures that produced stable emulsifications lasting longer than 30 min were selected.

Screening of Isolated Strains for their Ability to Form Biofilms on Silicate Surfaces Under Aerobic Conditions Sterile glass beads (3 mm, #11-312A, Fisher Scientific, Hampton, N.H.) were placed into the wells of a 24-well microtiterplate (#353047, BD Biosciences). Aliquots (1.0 mL) of either the Injection Water or the PPGAS medium (20 mM $NH_4Cl$, 20 mM KCl, 120 mM Tris-Cl, 1.6 mM $MgSO_4$, 1% peptone, 0.5% glucose, pH 7.5) containing 0.6% acetate or 0.6% lactate were added to each well. Samples (10 µL) of overnight microbial cultures were then added, and the plates were incubated at room temperature for up to one week. Glass beads were examined by microscopy directly in the microtiter wells.

Screening of Strains for their Ability to Form Biofilms on Silicate Surfaces Under Anaerobic Conditions.

To quantify the anaerobic formation of biofilms across different strains, a biofilm screening test was developed. Single colony isolates were grown anaerobically in 1.0 mL Injection Water supplemented with 1600 ppm sodium nitrate. Silica beads were added into the wells of a 96-well microtiterplate (#353070, BD Biosciences), and the cultures were divided into the wells at a final concentration of $OD_{600}$ of 0.01. Sodium acetate or sodium lactate (0.6% final concentration) was added. After eleven days of anaerobic incubation, the beads were removed from the wells, rinsed in sterile water, and transferred to a new microtiterplate. Crystal violet dye (75 µL, 0.05%) was added to each well, and the plate was incubated at room temperature for 5 min. The dye was then removed by washing each bead (×4) with 200 µL sterile water. To remove the bacteria from the beads and solubilize the remaining dye, 100 µL of 95% ethanol was added and samples were incubated at room temperature for 20 min with intermittent mixing. Aliquots (10 µL) were removed and added into 90 µL sterile water in a new microtiterplate. Absorbance of each sample at $OD_{590}$ was measured in a Victor3 (Perkin Elmer, Waltham, Mass.) plate reader to quantify the dye reflecting the relative concentrations of microorganisms that were attached to the silica beads.

Metabolism of Injection Water Organic Components

Injection water collected from North Slope oil wells was shipped cold on ice and stored in anaerobic conditions at 4° C. until used to test growth. Injection water was filtered (0.2 µm, washed, sterile polysulfone filter unit, Nalgene, Rochester, N.Y.), 10 mL was placed in a 20 mL-capacity glass vial, supplemented with $NaNO_3$ (final concentration 1.2 g/l nitrate) and sealed anaerobically. Duplicate test vials were set up for both the "no oil" and the "with oil" tests. Crude oil (5.0 mL) was added to the 10 mL of nitrate-supplemented injection water in "with oil" samples. Colonies were selected from aerobic agar plates, suspended in sterile distilled water and used to inoculate the vials. Incubations were done at room temperature with shaking (120 rpm). Available nitrate was monitored by ion chromatography as an indicator of cell growth.

Mini Sandpack Experiments to Observe Oil Release

Mini sandpack experiments were done in parallel in a multi-well apparatus similar to that described by J. D. Levi, et al. (*Intl. BioRes. J.,* 1, 336, 1985). A multiwell apparatus (FIG. 3) was constructed as follows: A five inch thick aluminum block (FIG. 3, (2)) was machined with a series of 5 inch long, ⅞ inch diameter holes (FIG. 3, (5)). In FIG. 3, four of these holes are shown although in subsequent tests a block with more holes was used. A 1 inch thick aluminum plate (FIG. 3, (1)) was machined with ¼ inch deep by 1 inch diameter wells. These wells were concentric with the holes machined into the 5 inch thick block. Small, ⅛ inch diameter holes (FIG. 3, (8)) were machined under the ¼ inch by 1 inch diameter wells and out to a side of the 1 inch thick block (FIG. 3, (1)). ⅛ inch pipe threads were machined into the outside face of the block and swagelock fittings (Swagelok Company) were mounted onto the side of the block to allow ⅛ inch tubing connections to these wells. These connectors were connected via ⅛ inch tubing to a series of syringe pumps—one pump being connected to each hole. A second 1 inch aluminum block (FIG. 3, (3)) was machined in the same manner. Two ⅛ inch thick neoprene rubber mats (FIG. 3, (4)) were cut the same size as the 1 inch thick blocks and ⅞ inch diameter holes with the same hole pattern as the blocks were cut into the rubber mats. Into each 1 inch thick plate (FIG. 3, (1) and (3)) was mounted a 1 inch diameter fritted glass filter (FIG. 3, (6)) (Chemglass Scientific Apparatus, Vineland, N.J.). This glass frit was sealed to each plate using a series of "O" rings (FIG. 3, (7)) (Parker Hannifin Corporation, O-Ring Division, Lexington, Ky.). The one inch thick plate with the syringe pump feed lines (FIG. 3, (1)) was covered with the neoprene gasket (FIG. 3, (4)), and the 5 inch thick block (FIG. 3, (2)) was bolted to the gasket (FIG. 3, (4)) in such a fashion that the wells in the bottom plate were in communication with the wells in the 5 inch thick block. All plates and equipment were sterilized by autoclaving prior to completing the assembly.

Six wells were then packed with an aged oil/sand mixed as follows: 403.2 mL of sterilized ocean sand (SX0076-1, LOT#46257714, EMD Chemicals Inc., Gibbstown, N.J.) was combined with 151.2 mL of the same sterile crude oil from the Alaskan North Slope. The oil and sand were combined under a nitrogen atmosphere and thoroughly mixed. This oil soaked sand mixture was aged for six days with additional mixing being done once or twice per day. This mixture was then packed into the six wells (FIG. 3, (5)) of the 5 inch block (FIG. 3, (2)). The second neoprene gasket (FIG. 3, (4)) was placed on the top of the 5 inch thick block and the second 1 inch thick plate (FIG. 3, (3)) with the glass frits (FIG. 3, (6)) and O ring seals (FIG. 3, (7)) as described for the other plate were bolted to the 5 inch block in such a way that the wells in the 1 inch plate were in communication with the wells that had the oil soaked sand packed into them. From the top of this second one inch plate, small holes were bored through the top and connected to ⅛ inch diameter tubing (FIG. 3, (9)). This tubing was run directly into a simple oil-water separator. This separator is very similar to that described in described by J. D. Levi, et al., supra. It consisted of a ⅛ inch diameter tube pushed through a bored out ⅛ inch by ½ inch tube reducer (Swagelok Company). This ⅛ inch diameter tube was placed concentric in a ½ inch Teflon tube that formed a stand leg for the oil/water separator. At the bottom of the Teflon tube, but below the top end of the ⅛ inch tube, was a "tee". The produced fluid from the sandpack was allowed to flow up through the ⅛ inch dip tube past the tee. The oil would float to the top of the stand leg above the tee. Water in the stand leg (vertical tube that acted as an oil collector) that was displaced went out the side port of the tee below the oil and up through a ⅛ inch flexible tube. This tube was configured so that it ran up to a height that was just below the top of the oil stand leg. This tube then was directed to a separate water collection jug. Thus the total height of liquid in the ½ inch oil stand leg was fixed, and oil that was released from the sandpack could be measured as the height of oil in the ½ inch diameter Teflon stand leg.

Identification of Plasmid Sequences

Plasmids were isolated by the QIAprep Miniprep procedure following the supplier's protocol (Qiagen, Valencia, Calif.). Plasmid DNA and Bluescript II SK+ cloning vector (Stratagene, La Jolla, Calif.) were restricted at 37° C. with either HindIII or EcoRI for 2 hr and gel purified. Bluescript vector DNA was dephosphorylated with calf intestine alkaline phosphatase following supplier's protocol (New England Biolabs, Beverly, Mass.). Restricted plasmid DNAs and respective dephosphorylated vector were ligated at room temperature for 30 min with T4 DNA ligase using standard protocols (New England Biolabs). TOP10 Oneshot chemically competent cells (Invitrogen, Carlsbad, Calif.) were transformed on ice for 30 min with 5 µL of the ligation reactions. Samples were streaked on LB plates containing 100 µg/ml ampicillin and 60 µg/ml 5-bromo-4-chloro-3-indolyl-b-D-galactopyranoside (X-gal) and grown overnight at 37° C. Colonies were picked and grown overnight in LB containing 100 µg/ml ampicillin. Plasmids were isolated by the QIAprep Miniprep (Qiagen, Valencia, Calif.) procedure and were sequenced using M13 forward and reverse primers (SEQ ID NOs: 7 and 8). Sequences were then assembled and aligned.

Automated Ribotyping

Automated ribotyping was used for conclusive identification of selected strains with similar 16S rDNA sequence phylogenetic characteristics (Bruce, J. L., 1996. *Food Technology*, 50, 77-81, 1996 and Sethi, M. R., *Am. Lab.* 5, 31-35, 1997). Ribotyping was performed as recommended by the manufacturer (DuPont Qualicon Inc., Wilmington, Del.). For these analyses, one fresh colony was picked, resuspended in the sample buffer and added to the processing module for the heat treatment step at 80° C. for 10 min to inhibit endogenous DNA-degrading enzymes. The temperature was then reduced, and two lytic enzymes (lysostaphin and N-acetyl-muramidase) (provided by the manufacturer) were added to the sample. The sample carrier was then loaded onto the Riboprinter system with the other commercial reagents. Restriction enzyme digestion using EcoRI enzyme, gel electrophoresis and blotting steps were completely automated. Briefly, bacterial DNA was digested with the EcoRI restriction enzyme and loaded onto an agarose gel: restriction fragments were separated by electrophoresis and simultaneously transferred to a nylon membrane. After a denaturation step, the nucleic acids were hybridized with a sulfonated DNA probe harboring the genes for the small and large rRNA subunits of *E. coli*. The hybridized probe was detected by capturing light emission from a chemiluminescent substrate with a charge-coupled device camera. The output consisted of a densitometric scan depicting the distribution of the EcoRI restriction fragments containing the 16S or 23S rDNA sequences and their molecular weights.

Bioremediation and Oil Pipeline Maintenance

The ability of *Pseudomonas stutzeri* LH4:15 to metabolize and mobilize or emulsify hydrocarbons makes this strain useful in the bioremediation of areas contaminated with hydrocarbons. Thus, also provided herein are methods for decontaminating or remediating contaminated areas by applying to the area(s) bacterial isolate *Pseudomonas stutzeri* LH4:15, which are then allowed to degrade the contaminants in situ. Bioremediation takes place when *Pseudomonas stutzeri* LH4:15 are exposed to hydrocarbons and converts them into products such as, e.g., carbon dioxide, water, and oxygen or when the growth of the LH4:18 cells allows release of high molecular weight hydrocarbons to the surface for subsequent removal by physical clean up processes. In some embodiments, *Pseudomonas stutzeri* LH4:15 can be incubated in the environment to be bioremediated without any added co-substrate, or other carbon or energy source. The bioremediation process can be monitored by periodically taking samples of the contaminated environment, extracting the hydrocarbons, and analyzing the extract using methods known to one skilled in the art.

Contaminated substrates that may be treated with *Pseudomonas stutzeri* LH4:15 include, but are not limited to, harbor dredge spoils, sediments, wastewater, sea water, soil, sand, sludge, air, and refinery wastes. In another embodiment, the contaminated substrate can be an oil pipeline. Hydrocarbon incrustation and sludge buildup are significant causes of decreased pipeline performance and can eventually lead to failure of the pipeline. Because of the ability of *Pseudomonas stutzeri* LH4:15 to degrade or release or emulsify hydrocarbons, application of LH4:15 to an oil pipeline containing incrusted hydrocarbons or hydrocarbon-containing sludge can be useful in the removal of the unwanted hydrocarbons from the pipeline.

In some embodiments, other agents effective in the bioremediation of hydrocarbons can be added to a *Pseudomonas stutzeri* LH4:15 bioremediation composition. These other agents may include a microorganism or more than one microorganism, such as a bacterium, a yeast, or a fungus. The agents may also include a chemical compound that is not lethal to *Pseudomonas stutzeri* LH4:15, but is effective at degrading or partially degrading hydrocarbons and/or other contaminants or stimulating growth of LH4:15 to effect oil release. In some embodiments, the additional agent is *Shewanella putrefaciens* strain LH4:18, which is described in the commonly owned, co-filed, and co-pending application (U.S. Ser. No. 12/105,690).

Microorganisms may be delivered to the contaminated substrate by any one of the many well known methods including those described in, e.g., Newcombe, D. A., and D. E. Crowley (Appl. Microbiol. Biotechnol. 51:877-82, 1999); Barbeau, C. et al. (Appl. Microbiol. Biotechnol. 48:745-52, 1997); U.S. Pat. Nos. 6,573,087, 6,087,155, and 5,877,014.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Anaerobic Growth of Bacterial Isolates on Oil as the Sole Carbon Source

To study growth of isolated colonies on crude oil as the sole carbon source under anaerobic conditions, purified isolates were inoculated into 20 mL-capacity serum vials containing 10 mL of the minimal salts medium (Table 3), 0.4 g/l sodium nitrate and 5.0 mL of autoclaved crude oil. The medium was deoxygenated by sparging the filled vials with a mixture of nitrogen and carbon dioxide followed by autoclaving. All manipulations of bacteria were performed in an anaerobic chamber (Coy Laboratories Products, Inc., Grass Lake, Mich.), and the cultures were incubated at ambient temperature with moderate shaking (100 rpm) for several weeks to several months and monitored for nitrate, nitrite, visible turbidity and visible oil modifications. When nitrate was depleted in any culture, sodium nitrate (50 g/l solution) was added to the medium to the final concentration of 0.4 g/l.

TABLE 3

MINIMAL SALTS MEDIUM

| Growth component | Final concentration | Chemical source |
|---|---|---|
| Nitrogen | 18.7 μM | $NH_4Cl$ |
| Phosphorus | 3.7 μM | $KH_2PO_4$ |
| Magnesium | 984 μM | $MgCl_2 \cdot 6H_2O$ |

TABLE 3-continued

MINIMAL SALTS MEDIUM

| Growth component | Final concentration | Chemical source |
|---|---|---|
| Calcium | 680 μM | $CaCL_2 \cdot 2H_2O$ |
| Sodium chloride | 172 mM | NaCl |
| Trace metals | 670 μM | nitrilotriacetic acid |
|  | 15.1 μM | $FeCl_2 \cdot 4H_2O$ |
|  | 1.2 μM | $CuCl_2 \cdot 2H_2O$ |
|  | 5.1 μM | $MnCL_2 \cdot 4H_2O$ |
|  | 12.6 μM | $CoCl_2 \cdot 6H_2O$ |
|  | 7.3 μM | $ZnCl_2$ |
|  | 1.6 μM | $H_3BO_3$ |
|  | 0.4 μM | $Na_2MoO_4 \cdot 2H_2O$ |
|  | 7.6 μM | $NiCl_2 \cdot 6H_2O$ |
| pH buffer (7.5 final) | 10 mM | Hepes |
| Selenium-tungstate | 22.8 nM | $Na_2SeO_3 \cdot 5H_2O$ |
|  | 24.3 nM | $Na_2WO_4 \cdot 2H_2O$ |
| Bicarbonate | 23.8 nM | $NaHCO_3$ |
| vitamins | 100 μg/l | vitamin B12 |
|  | 80 μg/l | p-aminobenzoic acid |
|  | 20 μg/l | nicotinic acid |
|  | 100 μg/l | calcium pantothenate |
|  | 300 μg/l | pyridoxine hydrochloride |
|  | 200 μg/l | thiamine-$HCl \cdot 2H_2O$ |
|  | 50 μg/l | alpha-lipoic acid |
| Electron acceptor | 0.4 g/l | $NaNO_3$ |

The pH of the medium was adjusted to 7.5.

Table 4 shows the results of these growth studies. Pure cultures which showed growth via nitrate reduction and turbidity increase under denitrifying conditions were chosen as "capable of growth on oil under denitrifying conditions". This subset was subjected to several tests for oil release phenomenon as described below. One strain, designated LH4:15, was identified by 16S rDNA typing as homologous to *Pseudomonas stutzeri*. A single colony of LH4:15 was inoculated into the medium described above containing 200 ppm of nitrate. This strain grew on oil as the sole source of carbon and depleted 100 ppm of nitrate in 60 days.

TABLE 4

NITRATE REDUCTION AS A MEASURE OF ANAEROBIC GROWTH WITH OIL AS THE SOLE CARBON SOURCE

| Bacterial isolate | % nitrate reduction | time to reduction (months) |
|---|---|---|
| *Marinobacterium* sp. LH4:4 | 0 |  |
| Unknown sp. LH4:7 | 0 |  |
| *Pseudomonas stutzeri* LH4:15 | 52 | 2 |
| *Shewanella putrefaciens* LH4:18 | 20 | 2 |
| *Thauera* sp. LH4:37 | 0 |  |
| Unknown sp. LH4:38 | 0 |  |
| *Pseudomonas stutzeri* MO LCED3 | 12 | 2 |

Example 2

Screening of Bacterial Isolates for Enhanced Oil Release

In this Example, a single colony of each isolated strain was used as the inoculum and grown to turbidity in the minimal salts medium defined in Table 3 with added 0.4% succinate as the carbon source. The concentration of each species was normalized to $OD_{600}$ of 1.0 or diluted 1:10 for a final $OD_{600}$ of 0.1. All operations for preparation of the micro sand columns, inoculation and growth were performed using sterile technique in an anaerobic glove bag. Inocula (4 mL) from either the OD$_{600}$ of 1.0 or OD$_{600}$ of 0.1 were added to small glass tubes and the micro sand columns immersed in the medium/cell mixtures with the narrow neck of the Pasteur pipets pointing up. The outer vials were sealed in the anaerobic chamber and allowed to incubate at ambient temperatures for 24 hr. Table 5 shows the strains tested and the observations of oil release after 24 hr.

TABLE 5

RELEASE OF OIL FROM MICROSAND COLUMNS BY ISOLATED BACTERIAL STRAINS.

| Bacterial isolate | inoculum OD600 = 1 | inoculum OD600 = 0.1 |
|---|---|---|
| Unknown sp. LH4:3 | n.d. | n.d. |
| Unknown sp. LH4:4 | no release | no release |
| Unknown sp. LH4:7 | no release | n.d. |
| Pseudomonas stutzeri LH4:15 | no release | oil release |
| Shewanella putrefaciens LH4:18 | oil release | no release |
| Thauera sp. LH4:37 | oil release | oil release |
| Unknown sp. LH4:38 | no release | no release |
| Pseudomonas stutzeri. MO LCED3 | no release | oil release |

Cultures were analyzed using their 16S rDNA profile to confirm their integrity and pure isolate conservation at several points in these studies. Pure isolates which had interesting attributes in these tests were further screened for oil release enhancement in a larger scale version of an oil well model as described in Example 8 and 9. *Pseudomonas stutzeri* LH4:15 was positive in this micro sandpack oil release test and was further studied for other useful attributes.

Example 3

Screening of Bacterial Isolates for Hydrophobicity

Since there is a direct correlation between cell surface hydrophobicity and surfactant production in many hydrocarbon-associated microbes, the purpose of this example was to test LH4:15 for hydrophobicity. The test was conducted as described above. FIG. 4 shows the results of the hydrophobicity testing of five different microbes. *Rhodococcus* sp. was used as the positive control for hydrophobicity. *Rhodococcus* species are known to have a highly hydrophobic surface (Bredholt, H. et al., Can. J. Microbiol., 48, 295-304, 2002). *Vibrio cyclotrophicus* was used as the negative control. Fluorescence was corrected for differences in OD across samples. As can be seen in FIG. 4, LH4:15 adhered to the polystyrene plate and had a relative fluorescence intensity comparable to that of the positive control indicating significant surface hydrophobicity. Due to its inherent hydrophobicity, strain LH4:15 was expected to have the ability to readily associate with hydrophobic hydrocarbons.

Example 4

Screening of Bacterial Isolates for their Ability to Stimulate Emulsion of Organics with Water Microorganisms synthesize a wide variety of biosurfactants and bioemulsifiers that lower surface and interfacial tensions and produce stable emulsions. An emulsification test was developed based on a modification of the BATH test as described above. Aliquots of the bacterial culture (500 μL) were mixed with 500 μL hexadecane in a sealed vial and agitated at high speed using a Vortex mixer for 1 min, and hexadecane emulsification was monitored over time. Those cultures that produced stable emulsifications lasting longer than 30 min were noted. FIG. 5 shows a stable oil-in-water emulsification for the *Rhodococcus* (control) sample and a stable water-in-oil emulsification for LH4:15 indicating the presence of bioemulsifiers in these samples.

Example 5

Screening Bacterial Isolates for their Ability to Form Biofilms

Figure 6:
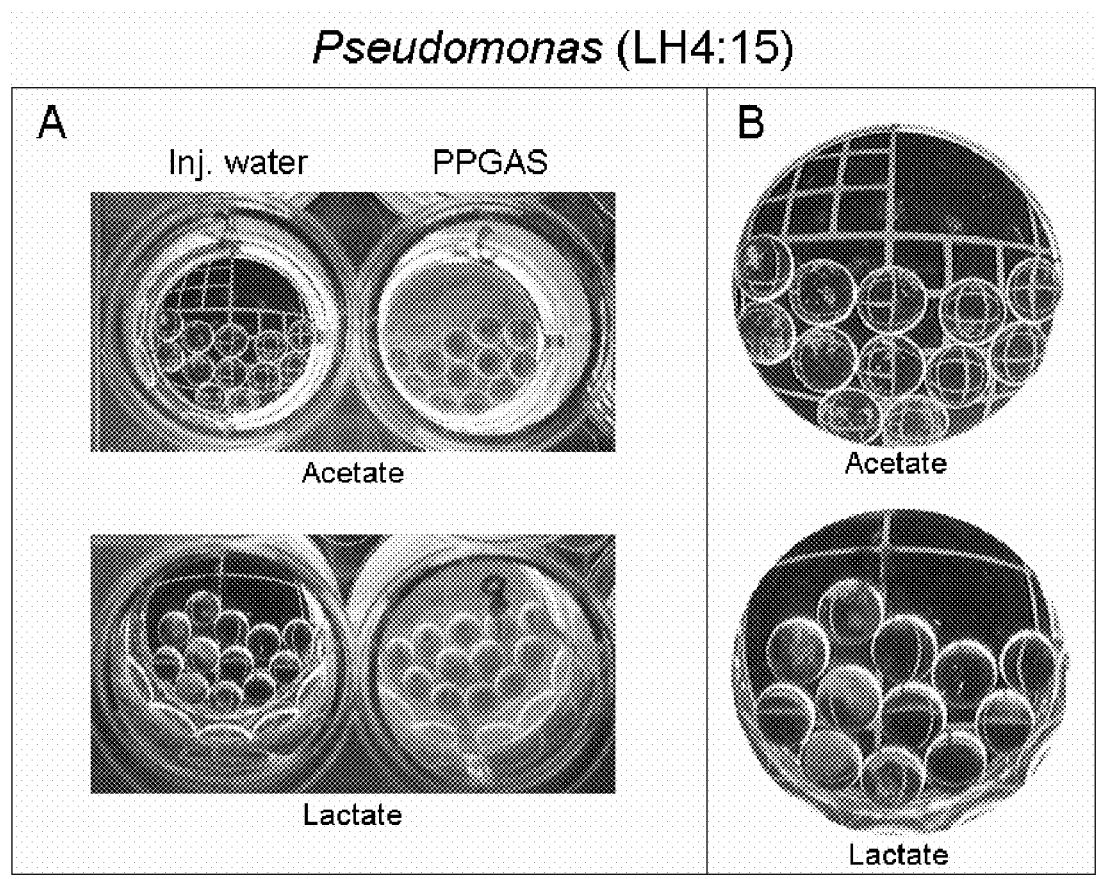

Numerous microorganisms are capable of adhering to and growing on a variety of surfaces and, in many cases, producing stable biofilms. Since biofilm formation is a potential mechanism for microbially enhanced oil recovery, Applicants assessed the ability of LH4:15 to produce stable biofilms on silica surfaces. Sterile glass beads (3 mm, #11-312A, Fisher Scientific, Hampton, N.H.) were placed into the wells of a 24-well microtiterplate (#353047, BD Biosciences). An aliquot (1.0 μl) of Injection Water or the PPGAS medium (20 mM NH$_4$Cl, 20 mM KCl, 120 mM Tris-Cl, 1.6 mM MgSO$_4$, 1% peptone, 0.5% glucose, pH 7.5) containing 0.6% acetate or lactate was added to each well followed by 10 μL of the overnight cultures, and the plates were incubated at room temperature for up to one week. FIG. 6 shows different types of biofilm formed on the glass beads. In Injection Water, the biofilms formed mostly on the glass beads with very little forming on the sides and bottom of the well. However, in the rich PPGAS medium, the biofilm formed throughout the entire well (FIG. 6A). Also, as can be seen in FIG. 6B, the biofilm formed in the presence of acetate was more granular whereas the biofilm formed in the presence of lactate was smoother. The results indicated that LH4:15 had the ability to readily form biofilms on silica surfaces and to produce different types of biofilms depending on the available carbon source.

Example 6

Screening Bacterial Isolates for their Ability to Form Anaerobic Biofilm on Silicate Surfaces To quantify the anaerobic formation of biofilms across different strains, a biofilm screening test was developed. Single colony isolates were grown anaerobically in 1.0 mL injection water supplemented with 1600 ppm sodium nitrate. Silica beads were added into the wells of a 96-well microtiterplate (#353070, BD Biosciences), the cultures were divided into the wells at a final concentration of OD$_{600}$ of 0.01, and sodium acetate or sodium lactate (final concentration 0.6%) was added. After eleven days of anaerobic growth, the beads were removed from the wells, rinsed in sterile water, and transferred to a new microtiterplate. Crystal violet dye (75 μL, 0.05%) was added to each well, and the plate was incubated at room temperature for 5 min. The beads were washed (4 times) with 200 μL sterile water to remove the dye, and the wash was removed by pipetting. To remove the bacteria from the beads and solubilize the dye, ethanol (100 μL, 95%) was added, and samples were incubated at room temperature for 20 min with intermittent mixing. Samples (10 μL) were removed and added into sterile water (90 μL) in a new microtiterplate. Absorbance of each sample was measured in a Victor3 (Perkin Elmer) plate reader at $OD_{590}$ to quantify the dye reflecting the relative concentrations of microorganisms that were attached to the silica beads.

FIG. 7 shows the results of the biofilm screening test. *Pseudomonas stutzeri* LH4:15 was among those that adhered to the silica particles and formed a biofilm. The results indicated that LH4:15 adhered to the beads more readily in the presence of acetate than lactate.

Example 7

Growth of Strains Utilizing Components of Injection Water

Anaerobic growth on organic material dissolved in the injection water would help maintain bacterial strains in the oil well environment, and is a desirable capability. The following Example shows that *Pseudomonas stutzeri* strain LH4:15 grows anaerobically in injection water via nitrate reduction.

Injection water plus nitrate was used to study growth of several bacterial strains as described above. Table 6 shows percent nitrate depletion in this test. In the presence of North Slope injection water, *Pseudomonas stutzeri* strain LH4:15 consumed 100% of the available nitrate in 9 days (Table 6), demonstrating that injection water alone could support growth of this strain. A number of other isolates, including *Ochrobactrum* sp. LH 4:45 and *Ochrobactrum* sp KW 1:29, showed similar behavior. In contrast a number of strains were strongly dependent on oil for metabolism. For example in cultures of *Azoarcus* sp. KW1:31, nitrate depletion nearly doubled in the presence of oil, and with strain Unknown sp. KW1:3, nitrate depletion required the presence of oil. The ability to metabolize dissolved material in the injection water demonstrates the ability of *Pseudomonas stutzeri* strain LH4:15 to remain active even in the absence of oil-derived carbon and energy sources.

TABLE 6

NITRATE DEPLETION BY VARIOUS TEST STRAINS. SHOWN IN DUPLICATE.
% $NO_3$ depleted after 9 days

| Strain # | no oil | with oil |
|---|---|---|
| Unknown sp. KW1:3-1 | 0 | 8 |
| Unknown sp. KW1:3-2 | 0 | 12 |
| *Ochrobactrum* sp. LH4:45-1 | 100 | 100 |
| *Ochrobactrum* sp. LH4:45-2 | 100 | 100 |
| *Ochrobactrum* sp. KW1:29-1 | 100 | 100 |
| *Ochrobactrum* sp. KW1:29-2 | 100 | 100 |
| *Shewanella putrefaciens* LH4:18-1 | 50 | 25 |
| *Shewanella putrefaciens* LH4:18-2 | 39 | 18 |
| *Pseudomonas stutzeri* LH4:15-1 | 100 | 100 |
| *Pseudomonas stutzeri* LH4:15-2 | 100 | 84 |
| *Azoarcus* HA. KW1:31-1 | 50 | 99 |
| *Azoarcus* HA. KW1:31-2 | 55 | 91 |

Example 8

Use of Mini Sandpacks for Studies on Oil Release with Mixed Cultures

Six continuous flow oil release tests were performed as described above to illustrate the oil release by mixed cultures of *Pseudomonas stutzeri* strain LH4:15 and *Shewanella putrefaciens* strain LH4:18. Strain LH4:18 is described in the commonly owned, co-filed, and co-pending application (U.S. Ser. No. 12/105,690). Three mini sandpacks were used as "uninoculated controls" while another three columns were identically inoculated using a mixture of both LH4:18 and LH4:15.

The six mini sandpacks were flooded with the synthetic brine 1 (Table 7), at a rate 3.0 ml/min for 6.6 pore volumes after which the flooding was stopped. The height of the oil in the stand legs was measured, and the amount of oil released relative to the original amount added was calculated.

The sandpacks were then either inoculated with cells of LH4:15 plus LH4:18 (as described below) or with live injection water from the same Alaskan North Slope field that the oil was obtained from as a control. Three mini sandpacks were inoculated with a mixture of LH4:18 and LH4:15. Each concentrated pure strain was diluted with filter sterilized injection water from the North Slope of Alaska to an $OD_{600}$ of 0.5. Equal volumes of these two diluted pure strains were combined, and the medium was augmented with 1.6 g/l of $NaNO_3$. This mixture was pumped into three of the mini sandpack columns for 0.92 pore volume. The three control mini sandpacks were inoculated with 0.92 pore volumes of live injection water from the North Slope of Alaska that had been augmented with 1.6 g/l of sodium nitrate. All flows were stopped and all six wells were allowed to sit for 19 days when brine 2 (Table 7) was pumped onto the mini sandpacks at a rate of 3.0 ml/hr for an additional 6.6 pore volumes. Periodically, the height of the oil in the stand legs was measured, and the amount of oil released relative to the original amount added was calculated. The average and the maximum additional oil released after inoculation were calculated. The results demonstrated the ability of *Pseudomonas stutzeri* LH4:15 to facilitate release of significant additional oil in a flow through experiment when combined with isolate *Shewenella putrefaciens* LH4:18 (FIG. 8).

TABLE 7

COMPONENTS OF BRINES 1 AND 2 USED IN MINI SANDPACK EXPERIMENTS

| Component | Brine 1 mg/l | Brine 2 mg/l |
|---|---|---|
| $NaHCO_3$ | 1377 | 1377 |
| $CaCl_2 \cdot 6H_2O$ | 394 | 394 |
| $MgCl_2 \cdot 6H_2O$ | 217 | 217 |
| $BaCl_2 \cdot 2H_2O$ | 32 | 32 |
| KCl | 90 | 90 |
| $SrCl_2 \cdot 6H_2O$ | 15 | 15 |
| LiCl | 6 | 6 |
| NaCl | 11560 | 11560 |
| $NaNO_3$ | 0 | 400 |

Example 9

Isolation and Identification of Plasmids in *Pseudomonas Stutzeri* LH4:15

Two plasmids of unknown function were identified in the *Pseudomonas stutzeri* LH4:15 isolate. This strain was grown to an approximate $OD_{600}$ of 1 in the PPGAS medium, and plasmids were isolated using the QIAprep Miniprep following the supplier's protocol (Qiagen, Valencia, Calif.). Plasmid DNA and Bluescript II SK+ cloning vector (Stratagene, La Jolla, Calif.) were restricted at 37° C. with either HindIII or coRI for 2 hr and gel purified. Bluescript vector DNA was dephosphorylated with calf intestine alkaline phosphatase following supplier's protocol (New England Biolabs, Beverly, Mass.). Restricted *Pseudomonas stutzeri* LH4:15 plasmid DNAs and respective dephosphorylated vector were ligated at room temperature for 30 min with T4 DNA ligase using standard protocols (New England Biolabs). TOP10 Oneshot chemically competent cells (Invitrogen, Carlsbad, Calif.) were transformed on ice for 30 min with 5 µL of the ligation reactions. Samples were streaked onto LB plates containing 100 µg/ml ampicillin and 60 µg/ml X-gal and grown overnight at 37° C. Colonies were selected and grown overnight in the LB medium containing 100 µg/ml ampicillin. Plasmids were isolated by the QIAprep Miniprep procedure and sequenced using M13 forward and reverse primers (SEQ ID NOs: 7 and 8). Sequences were then assembled and aligned. Walking primers (SEQ ID NOs: 3, 4, 5, 6) were designed and used to close the sequence gaps.

Plasmids LH4:15 pMP1 (2182 bp, SEQ ID NO:9) and LH4:15 pMP2 (2135 bp, SEQ ID NO:10) were assembled using Vector NTI. Plasmid LH4:15 pMP1 has partial identity (496/712, 69%) to *Pseudomonas stutzeri* S-47 plasmid p47S of unknown function. Plasmid LH4:15 pMP2 has partial identity (815/1019, 79%) to *Pseudomonas putida* plasmid pPP81 repA gene, ORFB, ORFC and ORFD.

Example 10

Screening of Pseudomonas Isolates for the Presence of Plasmids LH4:15 pMP1 and pMP2

To show that the *Pseudomonas stutzeri* LH4:15 isolate was distinct from other *Pseudomonas stutzeri* species, the presence of the two plasmids LH4:15 pMP1 and pMP2 in other *Pseudomonas stutzeri* species isolated from enrichment cultures was examined. The rDNA sequences of two of these isolates (LH4:13 and LH4:23) demonstrated 100% homology to strain LH4:15. Isolates (Table 8) were grown to an approximate $OD_{600}$ of 1 in the PPGAS medium. Samples of cultures (1.0 µL) were then subjected to PCR using primer pairs pr1f-1 and pr2r-1 or pr3f-1 and pr4r-1 (SEQ ID NOs: 3, 4, 5, 6), specific for LH4:15 pMP1 (SEQ ID NO:9) and LH4:15 pMP2 (SEQ ID NO:10), respectively. In addition, to confirm the efficiency of the amplification reactions, the rDNAs were also amplified using 1407R and 8F (SEQ ID NOs: 1, 2) primers to detect the 16S rDNA gene sequence. The PCR amplification mix included: 1.0× GoTaq PCR buffer (Promega), 0.4 mM dNTPs, 20 µmol of respective plasmid primer (or 25 µmol of each rDNA primer, 8F and 1407R), 0.5 µL of GoTaq polymerase (Promega) in a 50 µL reaction volume. The PCR thermocycling profile was as follows: 2 min at 95° C., followed by 35 cycles of: 1.5 min at 95° C., 1.5 min at 53° C., 2 min at 72° C., followed by a final extension step for 8 min at 72° C. using a Perkin Elmer 9600 thermocycler (Waltham, Mass.).

Table 8 shows the results of the plasmid amplification screen. A plus sign indicates that the target DNA was amplified. A minus sign indicates that the specific target was not amplified. As shown in the Table 8, isolate LH4:15 was the only microorganism that gave signals for both the LH4:15 pMP1 and pMP2 plasmids making it distinct from the other *Pseudomonas stutzeri* isolates even the ones with identical 16S rDNA gene sequences (LH4:13 and LH4:23).

TABLE 8

PCR FRAGMENTS DETECTED FOR pMP1, pMP2, AND 16S rDNA IN ISOLATED STRAINS OF *PSEUDOMONAS STUTZERI*

| *Pseudomonas stutzeri* Isolate identifier | Species ID (NCBI accession #) | pMP1 | pMP2 | 16S rDNA |
|---|---|---|---|---|
| LH4:15 | DQ224384.1 | + | + | + |
| LH4:13 | DQ224384.1 | − | − | + |
| LH4:20 | AJ312172.1 | − | − | + |
| LH4:23 | DQ224384.1 | − | − | + |
| LH4:24 | DQ288952 | − | − | + |
| LH4:26 | AJ312172.1 | − | + | + |

The particular culture described in this invention is *Pseudomonas stutzeri* strain LH4:15. To differentiate strain *Pseudomonas stutzeri* LH4:15 from other known *Pseudomonas stutzeri* strains with homologous 16S rDNA sequences, they were analyzed for the presence of extrachromosomal plasmids. As described in Examples 9 and 10, *Pseudomonas stutzeri* LH4:15 contains a set of two plasmids. Plasmid LH4:15 pMP1 has partial identity (496/712, 69%) to *Pseudomonas stutzeri* S-47 plasmid p47S of unknown function. Plasmid LH4:15 pMP2 has partial identity (815/1019, 79%) to *Pseudomonas putida* plasmid pPP81 repA gene, ORFB, ORFC and ORFD. These plasmids were not detected in other *Pseudomonas stutzeri* strains that were 100% homologous within the 16S rDNA sequence.

Example 11

Riboprinting To Determine Species Uniqueness

The 16S rDNA sequence used to determine taxonomy of isolate LH4:15 was 100% homologous to the 16S rDNA previously isolated species of *Pseudomonas stutzeri* strain 42a97, isolated from soil contaminated with mineral oil near a filling station in Northern Germany (Sikorski, J. et., supra). In order to determine that *Pseudomonas stutzeri* strain LH4:15 was a novel isolate, multiple strains of *Pseudomonas stutzeri* were subjected to automated Riboprinter™ analysis as described above. These additional strains were *Pseudomonas stutzeri* isolates LH4:13, LH4:20, LH4:23, LH4:24, and LH4:26, and *Pseudomonas stutzeri* ATCC strain BAA172 was used as a control. Strains LH4:13 and LH4:23 had 100% homology within the 16S rDNA gene sequences. However, using the riboprinter protocol (FIG. 9), it is clear that the pattern of EcoRI restriction fragments which hybridize to 16S and 23S rDNA probes is substantially different for LH4:15 than any of the other strains tested. LH4:23 and LH4:24 have similar fragment patterns as do LH4:13 and LH4:20. These analyses confirmed that the genomic sequences surrounding the 16S and 23 rDNA genes in LH4:15 are substantially different from the six tested strains underlining the uniqueness of strain *Pseudomonas stutzeri* LH4:15.

The invention claimed is:

1. A composition comprising a biologically pure microorganism designated as *Pseudomonas stutzeri* LH4:15 (ATCC No. PTA-8823).

2. The composition of claim 1, further comprising:
a) one or more electron acceptors; and
b) at least one carbon source.

3. The composition of claim 2, wherein said at least one carbon source comprises oil or an oil component.

4. The composition of claim 2, further comprising one or more additional microorganisms.

5. The composition of claim 4, wherein said one or more additional microorganisms are capable of growing on oil under denitrifying conditions.

6. The composition of claim 5, wherein said one or more additional microorganisms comprises a biologically pure microorganism designated as *Shewanella putrefaciens* LH4:18 (ATCC No. PTA-8822).

7. A method for improving oil recovery from an oil reservoir comprising:
a) providing a composition comprising as bacterial isolated a biologically pure microorganism designated as *Pseudomonas stutzeri* LH4:15 (ATCC No. PTA-8823), and minimal medium comprising simple nitrates capable of promoting the growth of said biologically pure microorganism; and
b) inoculating said reservoir with the composition of (a); wherein said growth of said biologically pure microorganism, under denitrifying conditions, in the oil reservoir promotes improved oil recovery.

8. The method of claim 7, wherein the composition of (a) further comprises one or more additional microorganisms capable of growing on oil under denitrifying conditions.

9. The method of claim 8, wherein said one or more additional microorganisms comprises a biologically pure microorganism designated as *Shewanella putrefaciens* LH4:18 (ATCC No. PTA-8822).

10. The method of claim 7, wherein said oil recovery is improved by said growth of said biologically pure microorganism designated as *Pseudomonas stutzeri* (ATCC No. PTA-8823) resulting in one or more of the following: (1) alteration of permeability of the subterranean formation to improve water sweep efficiency; (2) production of biosurfactants which decrease surface and interfacial tensions; (3) mediation of changes in wettability; (4) production of polymers which facilitate mobility of petroleum; (5) generation of gases that increase formation pressure; and (6) reduction of oil viscosity.

11. The method of claim 10, wherein the gases of (5) comprise $CO_2$.

12. A method for promoting hydrocarbon bioremediation comprising applying a biologically pure microorganism designated as *Pseudomonas stutzeri* LH4:15 (ATCC No. PTA-8823) to an area contaminated with hydrocarbons.

13. The method of claim 12, further comprising applying one or more additional microorganisms.

14. The method of claim 13, wherein said one or more additional microorganisms comprises a biologically pure microorganism designated as *Shewanella putrefaciens* LH4:18 (ATCC No. PTA-8822).

15. A method for promoting oil pipeline maintenance comprising applying a biologically pure microorganism designated as *Pseudomonas stutzeri* LH4:15 (ATCC No. PTA-8823) to an oil pipeline.

16. The method of claim 15, further comprising applying one or more additional microorganisms to said pipeline.

17. The method of claim 16, wherein said one or more additional microorganisms comprises a biologically pure microorganism designated as *Shewanella putrefaciens* LH4:18 (ATCC No. PTA-8822).

* * * * *